US009718865B2

(12) United States Patent
Kyle et al.

(10) Patent No.: US 9,718,865 B2
(45) Date of Patent: Aug. 1, 2017

(54) SODIUM CHANNEL BLOCKING PEPTIDES AND THE USE THEREOF

(71) Applicant: Purdue Pharma L.P., Stamford, CT (US)

(72) Inventors: Donald James Kyle, Yardley, PA (US); Jae Hyun Park, Princeton, NJ (US)

(73) Assignee: Purdue Pharma L.P., Stamford, CT (US)

(*) Notice: Subject to any disclaimer, the term of this patent is extended or adjusted under 35 U.S.C. 154(b) by 100 days.

(21) Appl. No.: 14/417,394

(22) PCT Filed: Jul. 26, 2013

(86) PCT No.: PCT/IB2013/001653
§ 371 (c)(1),
(2) Date: Jan. 26, 2015

(87) PCT Pub. No.: WO2014/016673
PCT Pub. Date: Jan. 30, 2014

(65) Prior Publication Data
US 2015/0191517 A1 Jul. 9, 2015

Related U.S. Application Data

(60) Provisional application No. 61/676,781, filed on Jul. 27, 2012.

(51) Int. Cl.

*A61K 38/16* (2006.01)
*C07K 14/435* (2006.01)
*A61K 38/00* (2006.01)

(52) U.S. Cl.

CPC ........ *C07K 14/43518* (2013.01); *A61K 38/00* (2013.01)

(58) Field of Classification Search
None
See application file for complete search history.

(56) References Cited

U.S. PATENT DOCUMENTS

2013/0296247 A1 11/2013 Park et al.
2014/0050720 A1* 2/2014 Smider et al. ............ 424/133.1

FOREIGN PATENT DOCUMENTS

WO WO 2012/004664 A1 1/2012

OTHER PUBLICATIONS

International Search Report mailed on Nov. 28, 2013 in corresponding International Application No. PCT/IB2013/001653 with Written Opinion.

Priest et al.,"ProTx-I and ProTx-II:Gat'ing modifiers of Vol tagegated Sodium Channels" ,TOXICON, 49: 194-201, (2007).

Anger, T., et al., "Medicinal Chemistry of Neuronal Voltage-Gated Sodium Channel Blockers," J. Med. Chem. 44(2):115-137, American Chemical Society, United States (2001).
Baker, M.D. and Wood, J.N., "Involvement of Na+ channels in pain pathways," Trends Pharmacol. Sci. 22(1):27-31, Elsevier Science Ltd., England (2001).
Beneng et al., "Sodium Channel Nav1.7 Immunoreactivity in Painful Human Dental Pulp and Burning Mouth Syndrome," BMC Neuroscience 11:1-7 (2010).
Black, J. A. et al., "Sensory Neuron-Specific Sodium Channel SNS Is Abnormally Expressed in the Brains of Mice with Experimental Allergic Encephalomyelitis and Humans with Multiple Sclerosis." Proceedings of the National Academy of Sciences of the United States of America 97.21 (2000): 11598-11602.
Boiko et al., "Compact Myelin Dictates the Differential Targeting of Two Sodium Channel Isoforms in the Same Axon," Neuron. 30: 91-104 (2001).
Cannon, S.C., "Spectrum of Sodium Channel Disturbances in the Nondystrophic Myotonias and Periodic Paralyses," Kidney Int. 57(3):772-779, International Society of Nephrology, United States (2000).
Catterall, W.A., "Common Modes of Drug Action on Na+ Channels: Local Anesthetics, Antiarrhythmics and Anticonvulsants," Trends Pharmacol. Sci. 8:57-65, Elsevier Science Publishers, B.V., Netherlands (1987).
Chahine, M., et al., "Voltage-Gated Sodium Channels in Neurological Disorders," CNS Neurol. Disord. Drug Targets 7(2):144-158, Bentham Science Publishers Ltd., United Arab Emirates (2008).
Clare, J.J., et al., "Voltage-Gated Sodium Channels as Therapeutic Targets," Drug Discov. Today 5(11):506-520, Elsevier Science Ltd., England (2000).
Donaldson, I., "Tegretol: a Double Blind Trial in Tinnitus," J. Laryngol. Otol. 95(9):947-951, Cambridge University Press, England (1981).
Edgerton et al, "Evidence for Multiple Effects of ProTxII on Activation Gating in NaV1.5," Toxicon 52:489-500 (2008).
Hubner, C.A. and Jentsch, T.J., "Ion Channel Diseases," Hum. Mol. Genet. 11(20):2435-2445, Oxford University Press, England (2002).
Kyle, D.J., and Ilyin, V.I., "Sodium Channel Blockers," J. Med. Chem. 50(11):2583-2588, American Chemical Society, United States (2007).
Lai, J., et al., "The Role of Voltage-Gated Sodium Channels in Neuropathic Pain," Curr. Opin. Neurobiol. 13(3):291-297, Elsevier Science Ltd., England (2003).
Lai, J., et al., "Voltage-Gated Sodium Channels and Hyperalgesia," Annu. Rev. Pharmacol. Toxicol. 44:371-397, Annual Reviews, United States (2004).

(Continued)

*Primary Examiner* — James H Alstrum Acevedo
*Assistant Examiner* — Sergio Coffa
(74) *Attorney, Agent, or Firm* — Purdue Pharma L.P.; Alan L. Koller; Weiying Yang

(57) ABSTRACT

The present invention relates to C-terminal modified Protoxin II peptides that selectively inhibit the Nav1.7 sodium channel; the present invention also relates to pharmaceutical compositions useful for prophylactic or therapeutic treatment of a disorder responsive to the blockade of sodium ion channels, especially Nav1.7 sodium ion channels; the present invention further provides methods of treating a disorder responsive to the blockade of sodium channels, and particularly Nav1.7 sodium channels, in a mammal suffering from excess activity of said channels.

19 Claims, 1 Drawing Sheet

(56) References Cited

OTHER PUBLICATIONS

Laird, J.M.A., et al., "Deficits in Visceral Pain and Referred Hyperalgesia in Nav1.8 (SNS/PN3)-Null Mice," J. Neurosci. 22(19):8352-8356, Society for Neuroscience, United States (2002).

Liu, H., et al., "Mutations in Cardiac Sodium Channels: Clinical Implications," Am. J. Pharmacogenomics 3(3):173-179, Adis Data Information BV, New Zealand (2003).

Majumdar, B., et al., "An Electrocochleographic Study of the Effects of Lignocaine on Patients with Tinnitus," Clin. Otolaryngol. Allied Sci. 8(3):175-180, Blackwell Scientific Publications, England (1983).

Meisler MH, and Kearney J.A., "Sodium Channel Mutations in Epilepsy and Other Neurological Disorders," J Clin Invest. 115(8):2010-2017, American Society for Clinical Investigation, United States (2005).

Middeleton et al., "Two Tarantula Peptides Inhibit Activation of Multiple Sodium Channels," Biochemistry 41:14734-14747 (2002).

Moller, A.R., "Similarities between Chronic Pain and Tinnitus," Am. J. Otol. 18(5):577-585, Lippincott-Raven, United States (1997).

Nassar, M.A., et al., "Nociceptor-Specific Gene Deletion Reveals a Major Role for Nav1.7 (PN1) in Acute and Inflammatory Pain," Proc. Natl. Acad. Sci. USA 101(34):12706-12711, National Academy of Sciences, United States (2004).

Noble, D., "Unraveling the Genetics and Mechanisms of Cardiac Arrhythmia," Proc. Natl. Acad. Sci. USA 99(9):5755-5756, National Academy of Sciences, United States (2002).

Rush et al., "Electrophysiological Properties of Two Axonal Sodium Channels," Nav1.2 and Nav1.6, Expressed in Mouse Spinal Sensory Neurones, 3: 803-815, J. PHYSIOL (2005).

Schmalhofer et al, "ProTx-II, a Selective Inhibitor of NaV1.7 Sodium Channels, Blocks Action Potential Propagation in Nociceptors," Molecular Pharm., 74:1476-1481 (2008).

Simpson, J.J. and Davies, W.E., "Recent Advances in the Pharmacological Treatment of Tinnitus," Trends Pharmacol. Sci. 20(1):12-18, Elsevier Science, England (1999).

Taylor, C.P. and Meldrum, B.S., "Na+ Channels as Targets for Neuroprotective Drugs," Trends Pharmacol. Sci. 16(9):309-316, Elsevier Science Ltd., England (1995).

Toledo-Aral, J.J., et al., "Identification of PN1, A Predominant Voltage-Dependent Sodium Channel Expressed Principally in Peripheral Neurons," Proc. Natl. Acad. Sci. USA 94(4):1527-1532, the National Academy of Sciences, United States (1997).

Tonndorf, J., "The Analogy between Tinnitus and Pain: A Suggestion for Physiological Basis of Chronic Tinnitus," Hearing Research 28(2-3):271-275, Elsevier Science Publishers B.V., Netherlands (1987).

Wood, J.N., et al., "Voltage-Gated Sodium Channels and Pain Pathways," J. Neurobiol. 61(1):55-71, Wiley Periodicals, Inc., United States (2004).

Yogeeswari, P., et al., "Ion Channels as Important Targets for Antiepileptic Drug Design," Curr. Drug Targets 5(7):589-602, Bentham Science Publishers Ltd., Netherlands (2004).

Edgerton el al.: "Inhibition of the activation pathway of the T-type calcium channel CaV3.1 by ProTxII" Toxicon, online Jun. 23, 2010, vol. 56, No. 4, pp. 624-636.

Klint el al.: "Spider-venom peptides that target voltage-gated sodium channels: Pharmacological tools and potential therapeutic leads" Toxicon, Apr. 7, 2012, vol. 60, No. 4, pp. 478-491.

Smith el al.: Molecular Interactions of the Gating Modifier Toxin ProTx-1i with Nav1.5: Implied Existence of a Novel Toxin Binding Site Coupled to Activation' The Journal of Biological Chemistry; Apr. 27, 2007; vol. 282, No. 17, pp. 12687-12697.

Xiao et al.: "The Tarantula Toxins ProTx-11 and Huwentoxin-IV Differentially Interact with Human Nav1.7 Voltage Sensors to Inhibit Channel Activation and Inactivation" Molecular Pharmacology, Dec. 2010, vol. 78, No. 6, pp. 1124-1134.

* cited by examiner

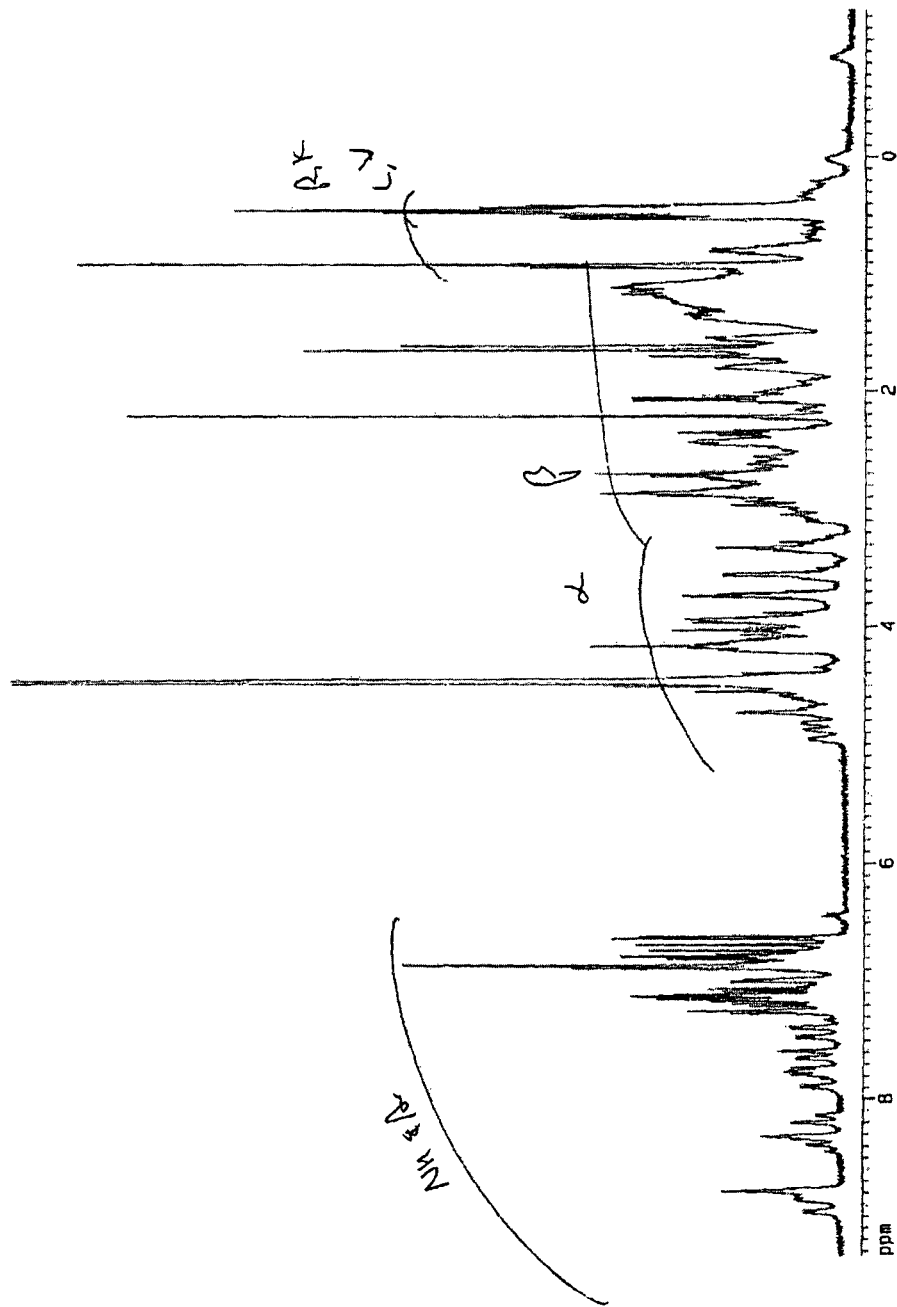

SODIUM CHANNEL BLOCKING PEPTIDES AND THE USE THEREOF

CROSS-REFERENCE TO RELATED APPLICATIONS

This application is the U.S. national phase, pursuant to 35 U.S.C. §371, of PCT International Application Ser. No. PCT/IB2013/001653, filed Jul. 26, 2013, designating the United States and published in English on Jan. 30, 2014 as publication WO 2014/016673 A1, which claims priority to U.S. Provisional Application Ser. No. 61/676,781, filed Jul. 27, 2012. The contents of the afore-mentioned patent applications are incorporated herein by their entirety.

FIELD OF THE INVENTION

This invention is in the field of medicinal chemistry. The invention relates to novel peptides that are C-terminal modified derivatives of Protoxin II and the use of these peptides as sodium ($Na^+$) channels blockers.

BACKGROUND ART

Voltage-gated sodium channels (VGSCs) are found in all excitable cells. In neuronal cells of the central nervous system (CNS) and peripheral nervous system (PNS), sodium channels are primarily responsible for generating the rapid upstroke of the action potential. In this manner, sodium channels are essential to the initiation and propagation of electrical signals in the nervous system. Proper function of sodium channels is therefore necessary for normal function of the neuron. Consequently, aberrant sodium channel function is thought to underlie a variety of medical disorders. See Hubner et al., *Hum. Mol. Genet.* 11:2435-2445 (2002) for a general review of inherited ion channel disorders, including epilepsy (Yogeeswari et al., *Curr. Drug Target* 5:589-602 (2004)), arrhythmia (Noble, *Proc. Natl. Acad. Sci. USA* 99:5755-5756 (2002)), myotonia (Cannon, *Kidney Int.* 57:772-779 (2000)), and pain (Wood et al., *J. Neurobiol.* 61:55-71 (2004)).

VGSCs are composed of one α-subunit, which forms the core of the channel and is responsible for voltage-dependent gating and ion permeation, and several auxiliary β-subunits (see e.g., Chahine et al., *CNS & Neurolog. Disorders-Drug Targets* 7:144-158 (2008) and Kyle and Ilyin, J. Med. Chem. 50:2583-2588 (2007)). The α-subunits are large proteins composed of four homologous domains. Each domain contains six α-helical transmembrane spanning segments. There are currently nine (9) known members of the family of VGSCs α-subunits, including SCNx, SCNAx, and $Na_v$x.x (see Table 1, below). The VGSC family has been phylogenetically divided into two subfamilies $Na_v$1.x (all but SCN6A) and $Na_v$2.x (SCN6A). The $Na_v$1.x subfamily can be functionally divided into two subgroups, those which are sensitive to blocking by tetrodotoxin (TTX-sensitive or TTX-s) and those which are resistant to blocking by tetrodotoxin (TTX-resistant or TTX-r).

TABLE 1

Voltage-Gated Sodium Channel Gene Family

| Type | Gene Symbol | Tissue Distribution | TTX $IC_{50}$ (nM) | Disease Association | Indications |
|---|---|---|---|---|---|
| $Na_v$1.1 | SCN1A | CNS/PNS | 10 | Epilepsy | Pain, seizures, neurodegeneration |
| $Na_v$1.2 | SCN2A | CNS | 10 | Epilepsy | Epilepsy, neurodegeneration |
| $Na_v$1.3 | SCN3A | CNS | 15 | — | Pain |
| $Na_v$1.4 | SCN4A | Skeletal muscle | 25 | Myotonia | Myotonia |
| $Na_v$1.5 | SCN5A | Heart muscle | 2,000 | Arrhythmia | Arrhythmia |
| $Na_v$1.6 | SCN8A | CNS/PNS | 6 | — | Pain, movement disorders |
| $Na_v$1.7 | SCN9A | PNS | 25 | Erythermalgia | Pain |
| $Na_v$1.8 | SCN10A | PNS | 50,000 | — | Pain |
| $Na_v$1.9 | SCN11A | PNS | 1,000 | — | Pain |

There are three members of the subgroup of TTX-resistant sodium channels. The SCN5A gene product ($Na_v$1.5) is almost exclusively expressed in cardiac tissue and has been shown to underlie a variety of cardiac arrhythmias and other conduction disorders (Liu et al., *Am. J. Pharmacogenomics* 3:173-179 (2003)). The remaining TTX-resistant sodium channels, $Na_v$1.8 (SCN10A, PN3, SNS) and $Na_v$1.9 (SCN11A, NaN, SNS2) are expressed in the peripheral nervous system and show preferential expression in primary nociceptive neurons. Aberrant expression of $Na_v$1.8 has been found in the CNS of human multiple sclerosis (MS) patients and also in a rodent model of MS (Black et al., *Proc. Natl. Acad. Sci. USA* 97:11598-115602 (2000)). Evidence for involvement in nociception is both associative (preferential expression in nociceptive neurons) and direct (genetic knockout). $Na_v$1.8-null mice exhibited typical nociceptive behavior in response to acute noxious stimulation but had significant deficits in referred pain and hyperalgesia (Laird et al., *J. Neurosci.* 22:8352-8356 (2002)).

The SCN2A gene product ($Na_v$1.2) is normally expressed along premyelinated and myelinated axons at different stages of maturation and is also expressed in a subset of demyelinated axons (Boiko et al., *Neuron* 30:91-104 (2001)). The $Na_v$1.2 may be a basis for the firing of action potentials, even with depolarization (Rush et al., *J. Physiol.* 3:803-815 (2005)). $Na_v$1.2 channels expressed in neurons are therapeutic targets in seizure, stroke, and pain.

The $Na_v$1.7 (PN1, SCN9A) VGSC is sensitive to blocking by tetrodotoxin and is preferentially expressed in peripheral sympathetic and sensory neurons. The SCN9A gene has been cloned from a number of species, including human, rat, and rabbit and shows about 90% amino acid identity between the human and rat genes (Toledo-Aral et al., *Proc. Natl. Acad. Sci. USA* 94:1527-1532 (1997)).

An increasing body of evidence suggests that $Na_v$1.7 sodium channel may play a key role in various pain states, including acute, inflammatory and/or neuropathic pain. For Example, $Na_v1.7$ sodium channel may play a role in inflammatory dental pain (Beneng et al., *BMC Neuroscience* 11:1-7 (2010)). Deletion of the SCN9A gene in nociceptive neurons of mice led to an increase in mechanical and thermal pain thresholds and reduction or abolition of inflammatory pain responses (Nassar et al., *Proc. Natl. Acad. Sci. USA* 101:12706-12711 (2004)).

Sodium channel-blocking agents have been reported to be effective in the treatment of various disease states, and have found particular use as local anesthetics, e.g., lidocaine and bupivacaine, and in the treatment of cardiac arrhythmias, e.g., propafenone and amiodarone, and epilepsy, e.g., lamotrigine, phenytoin and carbamazepine (see Clare et al., *Drug Discovery Today* 5:506-510 (2000); Lai et al., *Annu. Rev. Pharmacol. Toxicol.* 44:371-397 (2004); Anger et al., *J. Med. Chem.* 44:115-137 (2001), and Catterall, *Trends Pharmacol. Sci.* 8:57-65 (1987)). Each of these agents is believed to act by interfering with the rapid influx of sodium ions.

It has also been reported that sodium channel-blocking agents may be useful in the treatment of pain, including acute, chronic, inflammatory, neuropathic, and other types of pain such as rectal, ocular, and submandibular pain typically associated with paroxysmal extreme pain disorder (see, e.g., Kyle and Ilyin, *J. Med. Chem.* 50:2583-2588 (2007); Wood et al., *J. Neurobiol.* 61:55-71 (2004); Baker et al., *TRENDS in Pharmacol. Sci.* 22:27-31 (2001); and Lai et al., *Current Opinion in Neurobiol.* 13:291-297 (2003)).

It has further been reported that sodium channel-blocking agents may be useful in the treatment of neurological disorders such as epilepsy, seizures, epilepsy with febrile seizures, epilepsy with benign familial neonatal infantile seizures, inherited pain disorders, e.g., primary erythermalgia and paroxysmal extreme pain disorder, familial hemiplegic migraine, and movement disorder; and the treatment of other psychiatric disorders such as autism, cerebeller atrophy, ataxia, and mental retardation (see, e.g., Chahine et al., *CNS & Neurological Disorders-Drug Targets* 7:144-158 (2008) and Meisler and Kearney, *J. Clin. Invest.* 115:2010-2017 (2005)). In addition to the above-mentioned clinical uses, carbamazepine, lidocaine and phenytoin are used to treat neuropathic pain, such as from trigeminal neuralgia, diabetic neuropathy and other forms of nerve damage (Taylor and Meldrum, *Trends Pharmacol. Sci.* 16:309-316 (1995)). Furthermore, based on a number of similarities between chronic pain and tinnitus (Moller, *Am. J. Otol.* 18:577-585 (1997); Tonndorf, *Hear. Res.* 28:271-275 (1987)), it has been proposed that tinnitus should be viewed as a form of chronic pain sensation (Simpson et al., *Tip.* 20:12-18 (1999)). Indeed, lidocaine and carbamazepine have been shown to be efficacious in treating tinnitus (Majumdar et al., *Clin. Otolaryngol.* 8:175-180 (1983); Donaldson, *Laryngol. Otol.* 95:947-951 (1981)).

The polypeptide toxins from the tarantula *Thrixopelma pruriens* (protoxins) are members of the inhibitory cysteine-knot family of protein toxins, which contain 30 to 35 amino acid residues and three disulfide bridges. Protoxin I (ProTx I) and Protoxin II (ProTx II) are *T. pruriens* peptide toxins that inhibit activation of sodium channels (Middleton et al., *Biochemistry* 41:14734-14747 (2002)). ProTx I and ProTx II act as gating modifiers that prevent channel activation via a voltage sensor-trapping mechanism (Edgerton et al., *Toxicon* 52:489-500 (2008); Priest et al., *Toxicon* 49:194-201 (2007)). ProTx II inhibits $Na_v1.7$ sodium channels (see Schmalhofer et al., *Molecular Pharm.* 74: 1476-1481 (2008)).

WO 2012/004664 A2 discloses the analogs of sodium channel peptide toxin, and the pharmaceutically acceptable salts, prodrugs and solvates thereof. The analogs are useful as blockers of sodium (Na+) channels, and particularly $Na_v1.7$ channels. The entirety of WO 2012/004664 A2 is incorporated by reference herein.

WO 2012/004664 A2 discloses the following natural toxins and their sodium channel blocking properties:

TABLE 2

Natural Toxins Sodium Channel Assays

| Sequence* | SEQ ID NO: | Name | $IC_{50}$ $Na_v1.7$ (nm) | $IC_{50}$ $Na_v1.2$ (nm) |
|---|---|---|---|---|
| YCQKWMWTCDSERKCCEGMVCR LWCKKKLW | 1 | ProTx II | | 105 ± 20 |
| YCQKWMWTCDSARKCCEGLVCR LWCKKII | 2 | PaTx I | 423 ± 110 | 5000 |
| YCQKWMWTCDSERKCCEGYVCE LWCKYNL | 3 | JzTx XII | 1,527 ± 130 | 73,939 ± 14,440 |
| YCQKWLWTCDSERKCCEDMVCR LWCKKRL | 4 | GsAF I | 249 ± 20 | 255 ± 43 |
| YCQKWMWTCDSKRACCEGLRCK LWCRKII | 5 | JzTx V | 14 ± 10 | 157 ± 20 |
| YCQKWMWTCDEERKCCEGLVCR LWCKKKIEEG | 6 | VsTx II | 9,261 ± 2,210 | 42,409 ± 10,010 |
| YCQKWMWTCDEERKCCEGLVCR LWCKKKIEW | 7 | GsAF II | 70 ± 10 | 410 ± 20 |
| YCQKWMWTCDSKRKCCEDMVCQ LWCKKRL | 8 | GrTx I | 1,007 ± 600 | 2,690 ± 460 |

TABLE 2-continued

Natural Toxins Sodium Channel Assays

| Sequence* | SEQ ID NO: | Name | IC$_{50}$ Na$_v$1.7 (nm) | IC$_{50}$ Na$_v$1.2 (nm) |
|---|---|---|---|---|
| YCQKWMWTCDEERKCCEGLVCR LWCKRIINM | 9 | GsMTx II/ PaTX II | 260 ± 50 | 2,699 ± 790 |

*Contain 3 disulfide bridges in C1-C4, C2-C5 and C3-C6.

Amino acids and their abbreviations are listed in the following table.

| Amino Acid | 3 Letter Code | 1 Letter Code |
|---|---|---|
| Alanine | Ala | A |
| Glutamine | Gln | Q |
| Leucine | Leu | L |
| Serine | Ser | S |
| Arginine | Arg | R |
| Glutamic Acid/Glutamate | Glu | E |
| Lysine | Lys | K |
| Threonine | Thr | T |
| Asparagine | Asn | N |
| Glycine | Gly | G |
| Methionine | Met | M |
| Tryptophan | Trp | W |
| Aspartic Acid/Aspartate | Asp | D |
| Histidine | His | H |
| Phenylalanine | Phe | F |
| Tyrosine | Tyr | Y |
| Cysteine | Cys | C |
| Isoleucine | Ile | I |
| Proline | Pro | P |
| Valine | Val | V |

WO 2012/004664 A2 also discloses a C-terminal modified Protoxin II analog (SEQ ID NO: 10):

This analog shows similar potency to Na$_v$1.7 as unmodified Protoxin II, but decreased selectivity for Na$_v$1.7 over Na$_v$1.2 as compared to unmodified Protoxin II:

| Sequence* | SEQ ID NO: | Name | IC$_{50}$ Na$_v$1.7 (nm) | IC$_{50}$ Na$_v$1.2 (nm) |
|---|---|---|---|---|
| YCQKWMWTCDSERKCCEGMVCRLWCK KKLW-NH$_2$ | 10 | Protoxin II-NH$_2$ | 1 | 8 ± 1 |
| YCQKWMWTCDSERKCCEGMVCRLWCK KKLW | 1 | Protoxin II | 1 | 105 + 20 |

*Contain 3 disulfide bridges in C1-C4, C2-C5 and C3-C6.
See WO 2012/004664 A2, Tables 2 and 3. The loss of selectivity is undesirable.

BRIEF SUMMARY OF THE INVENTION

It has been discovered that novel peptides that are C-terminal modified derivatives of Protoxin II have higher potency to Na$_v$1.7 than that of Protoxin II, while maintaining the selectivity for Na$_v$1.7 over Na$_v$1.2. This is surprising and unexpected in view of the state of art.

The present invention provides C-terminal modified Protoxin II peptides of formula (I) disclosed herein, and pharmaceutically acceptable salts, prodrugs and solvates thereof, which are useful as blockers of sodium (Na$^+$) channels, and particularly Na$_v$1.7 channels. These peptides show selectivity as Na$_v$1.7 channel blockers relative to Na$_v$1.2.

The present invention further provides pharmaceutical compositions comprising an effective amount of at least one C-terminal modified Protoxin II peptides of formula (I), or a pharmaceutically acceptable salt, prodrug or solvate thereof, in a mixture with one or more pharmaceutically acceptable carriers. Pharmaceutical compositions of the present invention are useful for treating or preventing a disorder responsive to the blockade of sodium ion channels, especially Na$_v$1.7 sodium ion channels.

The present invention further provides a method of treating a disorder responsive to the blockade of sodium channels, and particularly Na$_v$1.7 sodium channels, in a mammal suffering from excess activity of said channels. The method comprises administering to said mammal an effective amount of at least one C-terminal modified Protoxin II peptides, or a pharmaceutically acceptable salt, prodrug or solvate thereof, as described herein. In a preferred embodiment, the disorder being treated is pain (e.g., acute pain, chronic pain, or inflammatory pain, which includes but is not limited to, neuropathic pain and surgical pain).

The present invention further provides a method of prophylactic or therapeutic treatment of a disorder responsive to the blockade of sodium channels, and particularly Na$_v$1.7 sodium channels, in a mammal at risk of suffering from excess activity of said channels. The method comprises administering to said mammal an effective amount of at least one C-terminal modified Protoxin II peptide of formula (I), or a pharmaceutically acceptable salt, prodrug or solvate thereof, as described herein. In a preferred embodiment, the disorder being prevented is pain (e.g., acute pain, chronic pain, or inflammatory pain, which includes but is not limited to, neuropathic pain and surgical pain).

The present invention further provides the use of C-terminal modified Protoxin II peptides of formula (I), or a pharmaceutically acceptable salt, prodrug or solvate thereof, in the manufacture of a medicament useful to treat or prevent a disorder responsive to the blockade of sodium channels, and particularly $Na_v1.7$ sodium channels. In a preferred embodiment, the disorder being treated or prevented is pain (e.g., acute pain, chronic pain, or inflammatory pain, which includes but is not limited to, neuropathic pain and surgical pain).

The present invention further provides a method of modulating the activity of sodium ion channels, especially $Na_v1.7$ sodium ion channels, in a cell, or in a membrane preparation, which method comprises contacting the cell or membrane preparation with an effective amount of at least one C-terminal modified Protoxin II peptide of formula (I), or a pharmaceutically acceptable salt, prodrug or solvate thereof. In certain embodiments, the method is carried out in an in vitro cellular or membrane assay system. In other embodiments, the method is carried out in an in vivo system, e.g., in a mammal such as a human.

The present invention further provides a radiolabeled or fluorescently labeled C-terminal modified Protoxin II peptide of formula (I), its salt, prodrug or solvate, and the use of such a radiolabeled or fluorescently labeled peptide as a ligand for use in any appropriately selected competitive binding assays and screening methodologies. Thus, the present invention further provides a method for screening a candidate peptide for its ability to bind to a sodium channel or sodium channel subunit using a radiolabeled or fluorescently labeled peptide of the present invention. In certain embodiments, the peptide is radiolabeled with $^3H$, $^{11}C$ or $^{14}C$. This competitive binding assay can be conducted using any appropriately selected screening methodology.

It is to be understood that both the foregoing summary and the following detailed description are exemplary and explanatory only and are not necessarily restrictive of the invention as claimed.

BRIEF DESCRIPTION OF DRAWINGS

FIG. 1 provides a proton NMR trace of Protoxin II-NHMe.

DETAILED DESCRIPTION OF THE INVENTION

As used herein, the singular terms "a" and "the" are synonymous and used interchangeably with "one or more" and "at least one," unless the language and/or context clearly indicates otherwise. As used herein, the term "comprising" means including, made up of, and composed of. All numbers in this description indicating amounts, ratios of materials, physical properties of materials, and/or use are to be understood as modified by the word "about," except as otherwise explicitly indicated. The term "isolated" in the context of the present invention indicates that a peptide has been removed from its natural environment and/or is presented in a form in which it is not found in nature.

Some of the peptides of the present invention may contain one or more chiral centers and may thus give rise to enantiomers, diastereomers, and other stereoisomeric forms. The present disclosure is meant to encompass all such possible forms, as well as their racemic and resolved forms and mixtures thereof. The individual enantiomers can be separated according to methods known in the art in view of the present disclosure. The term "chiral center" refers to a carbon atom to which four different groups are attached.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction. The term "racemic" refers to a mixture of equal parts of enantiomers and which mixture is optically inactive.

As used herein, a "prodrug" of a C-terminal modified Protoxin II peptide of the present invention is converted to the peptide of the present invention via an enzymatic reaction, typically under physiological conditions in the living body, that is, conversion from the prodrug to the peptide of the present invention occurs by enzymatically catalyzed oxidation, reduction, or hydrolysis, etc. Methods for making peptide prodrugs are known in the art. See, e.g., Oliyai, R., *Advanced Drug Delivery Reviews* 19:275-286 (1996); Oliyai et al., *Ann. Rev. Pharmcol. Toxicol.* 32:521-44 (1993); Paulette et al., *Advanced Drug Delivery Reviews* 27:235-256 (1997); Han, H.-K., *AAPS Pharmsci.* 2:1-11 (2000); and Prokai, L., *Expert Opinion On Therapeutic Patents* 7:233-245 (1997).

The present invention is based on the use of C-terminal modified Protoxin II peptides and the pharmaceutically acceptable salts, prodrugs and solvates thereof, as blockers of $Na^+$ channels. In view of this property, peptides of the invention are useful for treating or preventing disorders that can be treated or prevented by the blockade of sodium ion channels. In one aspect, peptides of the invention selectively block $Na_v1.7$ sodium ion channels compared to other sodium channels, e.g., $Na_v1.2$, and are therefore useful for treating or preventing disorders responsive to the selective blockade of $Na_v1.7$ sodium ion channels.

In one embodiment, peptides of the present invention exhibit selectivity for $Na_v1.7$ sodium channels over $Na_v1.2$ sodium channels in electrophysiological assays described herein. The phrase "selectivity for $Na_v1.7$ sodium channels over $Na_v1.2$ sodium channels" is used herein to mean that the ratio of an $IC_{50}$ for $Na_v1.7$ sodium channel blocking activity for a peptide of the invention over an $IC_{50}$ for $Na_v1.2$ sodium channel blocking activity for the same peptide is less than 1, i.e., $Na_v1.7$ $IC_{50}/Na_v1.2$ $IC_{50}<1$. Preferably, the C-terminal modified Protoxin II peptides of the present invention exhibit a $Na_v1.7$ $IC_{50}/Na_v1.2$ $IC_{50}$ ratio of about 1/2, 1/3, 1/4, 1/5, 1/6, 1/7, 1/8, 1/9, 1/10, 1/15, 1/20, 1/25, 1/30, 1/35, 1/40, 1/45, 1/50, 1/55, 1/60, 1/65, 1/70, 1/75, 1/80, 1/85, 1/90, 1/95, 1/100, 1/125, 1/150, 1/175, 1/200, 1/225, 1/250, 1/275, 1/300, 1/325, 1/350, 1/375, 1/400, 1/425, 1/450, 1/475 or 1/500 or less.

More preferably, the C-terminal modified Protoxin II peptides of the present invention exhibit a $Na_v1.7$ $IC_{50}/Na_v1.2$ $IC_{50}$ ratio of about 1/4, 1/5, 1/6, 1/7, 1/8, 1/9, 1/10, 1/15, 1/20, 1/25, 1/30, 1/35, 1/40, 1/45, 1/50, 1/55, 1/60, 1/65, 1/70, 1/75, 1/80, 1/85, 1/90, 1/95, 1/100, or less.

The present invention provides a C-terminal modified Protoxin II peptide of the following general formula (I):

$$\text{Pro}\diagdown\underset{\diagup}{\overset{O}{\|}}\diagdown XR_1,\qquad(I)$$

or a pharmaceutically acceptable salt, prodrug or solvate thereof,
wherein:
Pro is Protoxin II having the amino acid sequence: $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Glu_{12}$-$Arg_{13}$-$Lys_{14}$-$Cys_{15}$-$Cys_{16}$-$Glu_{17}$-$Glyl_{18}$-$Met_{19}$-$Val_{20}$-$Cys_{21}$-$Arg_{22}$-$Leu_{23}$-$Trp_{24}$-$Cys_{25}$-$Lys_{26}$-$Lys_{27}$-$Lys_{28}$-$Leu_{29}$-$Trp_{30}$ (SEQ ID NO: 1), wherein $Trp_{30}$ is D or L-$Trp_{30}$,
X is —NH— or —O—, and
$R_1$ is $C_1$-$C_6$ alkyl, or $C_3$-$C_7$ cycloalkyl, or $C_5$-$C_{10}$ aryl, or when X is —NH—, $R_1$ is —CH(R)—COOH, wherein R is selected from a group consisting of —H, —$CH_3$, —$CH_2CH_2CH_2$—NH—$C(NH_2)$=NH, —$CH_2CONH_2$, —$CH_2COOH$, —$CH_2CH_2COOH$, —$CH_2SH$, —$CH_2CH_2CONH_2$, —$CH(CH_3)CH_2CH_3$, —$CH_2CH(CH_3)_2$, —$CH(CH_3)_2$, —$CH_2CH_2CH_2NH_2$, —$CH_2CH_2SCH_3$, —$CH_2C_6H_6$, —$CH_2OH$, —$CH(OH)CH_3$,

[chemical structures: indol-2-ylmethyl, imidazol-5-ylmethyl, and 4-hydroxybenzyl groups]

For the purpose of the present disclosure, the term "alkyl" as used herein refers to a straight- or branched-chain aliphatic hydrocarbon. Non limiting exemplary $C_1$-$C_6$ alkyl groups include methyl, ethyl, propyl, isopropyl, butyl, sec-butyl, tert-butyl, iso-butyl, 1-pentyl, hexyl, and the like. In one embodiment, $R_1$ is methyl, ethyl or propyl. In another embodiment, $R_1$ is methyl. In another embodiment, $R_1$ is ethyl. In another embodiment, $R_1$ is propyl.

For the purpose of the present disclosure, the term "cycloalkyl" as used herein refers to optionally substituted cyclic aliphatic hydrocarbons containing one or two rings. Non-limiting exemplary substituents include alkyl, —O-alkyl, halogen, or hydroxyl group. Non-limiting exemplary $C_3$-$C_7$ cycloalkyl groups include cyclopropyl, cyclobutyl, cyclopentyl, cyclohexyl, cycloheptyl, and the like. In one embodiment, $R_1$ is cyclopentyl, cyclohexyl, or cycloheptyl. In another embodiment, $R_1$ is cyclohexyl.

For the purpose of the present disclosure, the term "aryl" as used herein refers to optionally substituted monocyclic and bicyclic aromatic ring systems having 0, 1, 2, 3, or 4 heteroatoms independently chosen from oxygen, nitrogen and sulfur. Non-limiting exemplary substituents include alkyl, —O-alkyl, halogen, or hydroxyl group. Non-limiting exemplary $C_5$-$C_{10}$ aryl groups include phenyl, naphthyl, thienyl, furyl, benzofuryl, pyranyl, pyrrolyl, imidazolyl, pyrazolyl, pyridyl, or pyrimidinyl. In one embodiment, $R_1$ is phenyl or substituted phenyl. In another embodiment, $R_1$ is phenyl.

In one embodiment, $Trp_{30}$ is D-Trp. In another embodiment, $Trp_{30}$ is L-Trp.

In one embodiment, $R_1$ is a group having the following formula:

[chemical structure: indol-3-yl-methyl with α-methyl carboxylic acid]

In one embodiment, $R_1$ is a group having the following formula:

[chemical structure: (S)-configured indol-3-yl-methyl α-methyl carboxylic acid]

In another embodiment, $R_1$ is a group having the following formula:

[chemical structure: (R)-configured indol-3-yl-methyl α-methyl carboxylic acid]

In one embodiment, X is —NH and $R_1$ is —CH(R)—COOH. In one embodiment, the C-terminal modified Protoxin II peptides are recombinantly expressed. In another embodiment, the C-terminal modified Protoxin II peptides are chemically synthesized.

The present invention also provides a composition comprising a C-terminal modified Protoxin II peptides of formula (I), or a salt, prodrug or solvate thereof, and a pharmaceutically acceptable carrier or diluent. In one embodiment, the composition is a sterile composition.

The present invention also provides a container comprising a C-terminal modified Protoxin II peptide of formula (I), or a salt, prodrug or solvate thereof. In one embodiment, the container is a vial. In another embodiment, the container is an intravenous fluid delivery container, e.g., a bag, a tubing, or a cartridge, each of which can be adapted for use with a mechanized analgesic delivery system, such as a pump.

The present invention also provides an article of manufacture comprising a plurality of containers, each of which contains a pharmaceutical composition of the present invention.

The invention disclosed herein also encompasses any of the disclosed C-terminal modified Protoxin II peptides being isotopically-labelled (e.g., radiolabeled) by having one or more atoms thereof replaced by an atom having a different atomic mass or mass number. Examples of isotopes include but are not limited to isotopes of hydrogen, carbon, nitrogen, oxygen, phosphorous, fluorine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, and $^{36}$Cl, respectively, and preferably $^3$H, $^{11}$C, and $^{14}$C. Isotopically-labeled C-terminal modified Protoxin II peptides can be prepared by methods known in the art in view of this disclosure.

The invention disclosed herein is also intended to encompass C-terminal modified Protoxin II peptides of the present invention that have been fluorescently labeled or labeled with Europium or a Europium-based label.

The present invention also provides the use of any of the radiolabeled or fluorescently labeled C-terminal modified Protoxin II peptides of the invention as detectably labeled ligands to bind to the sodium channel. One use of such labeled peptides is the characterization of specific receptor binding. Another use of such labeled peptides is as an alternative to animal testing for the evaluation of chemical structure-activity relationships.

The invention disclosed herein also encompasses the preparation and use of salts of the disclosed C-terminal modified Protoxin II peptides of formula (I), including all pharmaceutically acceptable salts of the disclosed C-terminal modified Protoxin II peptides. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate or the like.

Acid addition salts can be formed by mixing a solution of the particular C-terminal modified Protoxin II peptide of formula (I) of the invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the C-terminal modified Protoxin II peptides of formula (I) of the invention with a solution of a pharmaceutically acceptable non-toxic base such as sodium hydroxide, potassium hydroxide, choline hydroxide, sodium carbonate or the like.

The invention disclosed herein is also meant to encompass solvates of any of the disclosed C-terminal modified Protoxin II peptides of formula (I) of the invention. Solvates typically do not significantly alter the physiological activity or toxicity of the peptides, and as such may function as pharmacological equivalents. The term "solvate" as used herein is a combination, physical association and/or solvation of a peptide of the invention with a solvent molecule such as, e.g. a disolvate, monosolvate or hemisolvate, where the ratio of solvent molecule to peptide is typically 2:1, 1:1 or 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Peptides of the invention may be unsolvated, or may be solvated with a pharmaceutically acceptable solvent such as water, methanol, ethanol, and the like. One type of solvate is a hydrate. A "hydrate" relates to a particular subgroup of solvates where the solvent molecule is water. Methods for preparing solvates are generally known in the art. See, for example, Caira et al., *J. Pharmaceut. Sci.*, 93(3):601-611 (2004), which describes the preparation of solvates of fluconazole with ethyl acetate, and with water. Similar preparation of solvates, hemisolvates, hydrates, and the like are described by Tonder et al., *AAPS Pharm. Sci. Tech.*, 5(1):Article 12 (2004), and Bingham et al., *Chem. Commun.*: 603-604 (2001). A typical, non-limiting, process of preparing a solvate would involve dissolving a peptide of the invention in a desired solvent (organic, water, or a mixture thereof) at temperatures above about 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

The present invention also provides a method for treating or preventing a disorder responsive to the blockade of sodium channels, and particularly the selective blockade of $Na_v1.7$ sodium channels, in a subject suffering from, or at risk of suffering from the disorder, the method comprises administering to the subject an effective amount of a C-terminal modified Protoxin II peptide of formula (I), or a salt, prodrug or solvate thereof.

In one embodiment, the present invention provides a method of treating pain (palliative treatment). In another embodiment, the present invention provides a method of preventing pain (pre-emptive treatment). In one embodiment, the type of pain treated is chronic pain. In another embodiment, the type of pain treated is acute pain. In another embodiment, the type of pain treated is neuropathic pain. In another embodiment, the type of pain treated is inflammatory pain. In another embodiment, the type of pain treated is surgical pain. In each instance, such method of treatment or prevention requires administering to a subject in need of such treatment or prevention an amount of a C-terminal modified Protoxin II peptide of formula (I) of the invention that is therapeutically effective in achieving said result. In one embodiment, the amount of such C-terminal modified Protoxin II peptides of formula (I) is the amount that is effective to substantially block sodium channels in vivo.

Chronic pain includes, but is not limited to, inflammatory pain, neuropathic pain, postoperative pain, cancer pain, osteoarthritis pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgia, neuropathic, and idiopathic pain syndromes.

The methods of the present invention may be used to treat or prevent chronic somatic pain, which generally results from inflammatory responses to tissue injury such as nerve entrapment, surgical procedures, cancer or arthritis (Brower, *Nature Biotechnology* 18:387-391(2000)). Inflammatory pain includes, but is not limited to, pain associated with osteoarthritis and rheumatoid arthritis.

The methods of the present invention may be used to treat or prevent chronic neuropathic pain, which is a heterogenous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. Chronic pain is different from acute pain in that patients suffering from chronic pain suffer the abnormal pain sensations that can be described as spontaneous pain, continuous superficial burning and/or deep aching pain. The pain can be evoked by heat-, cold-, and mechano-hyperalgesia or by heat-, cold-, or mechano-allodynia.

The methods of the present invention may be used to treat or prevent neuropathic pain, which can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can also cause nerve injury. Neuropathic pain includes but is not limited to pain caused by nerve injury such as, for example, the pain from which diabetics suffer.

In one embodiment, the subject being treated by a method of the present invention is a mammal. In another embodiment, the mammal is a human.

In one embodiment, a C-terminal modified Protoxin II peptide of formula (I) of the invention is administered to the subject by any suitable route of administration, including by one or more of the oral, buccal, mucosal, sublingual, parenteral, subcutaneous, intramuscular, intraperitoneal, intrathecal, intranasal, inhalation, transdermal, rectal or vaginal routes of administration.

The present invention is also directed to the use of a C-terminal modified Protoxin II peptide of formula (I) of the invention in the manufacture of a medicament for modulating sodium channels, especially $Na_v1.7$ sodium channels, in an in vitro or in vivo system.

The present invention is also directed to the use of a C-terminal modified Protoxin II peptide of formula (I) of the invention in the manufacture of a medicament for treating a disorder or providing preemptive or palliative treatment of a disorder that is responsive to the blockade of sodium channels (e.g., any of the disorders listed above) in a subject suffering from said disorder. In one embodiment, the disorder is responsive to the selective blockade of $Na_v1.7$ sodium channels.

Synthesis of C-Terminal Modified Protoxin II Peptides

The peptides of the invention can be synthesized using peptide synthesis methodologies, in which amino acids are linked by peptide bonds, and other chemical synthetic procedures, as known in the art and in view of this disclosure, e.g., Atherton, E. and Sheppard, R. C., "*Solid Phase Peptide Synthesis: A Practical Approach*," IRL Press. (1989). Non-limiting examples of solid-phase synthesis are Fmoc solid-phase synthesis, and t-boc solid phase synthesis.

The peptides of the invention can be obtained according the following general scheme:

\* Boc-Tyr(tBu)—OH was used for the last amino acid (Tyr)

Fmoc-L-amino acids are available from Protein Technologies, Inc. (Tucson, Ariz., U.S.A.). H-Trp(Boc)-2-Cl-Trt resin is available from AnaSpec Inc. (Fremont, Calif., U.S.A.). 2-(7-Aza-1H-benzothazole-1-yl)-1,1,3,3-tetramethyluronium hexafluorophosphate ("HATU") is available from Genscript Corp. (Piscataway, New Jersey, U.S.A.) HPLC-graded solvents and ReagentPlus®-graded reagents, e.g., acetic acid ("AcOH"), trifluoroethanol ("TFE"), 2,4,6-trimethylpyridine ("2,4,6-collidine"), dichloromethane ("DCM"), trifluoroacetic acid ("TFA"), triisopropylsilane ("TIS"), 3,6-Dioxa-1,8-octanedithiol, and thioanisole, are available from Sigma-Aldrich (St. Louis, Mo., U.S.A.).

Testing of C-Terminal Modified Protoxin II Peptides

The peptides of the invention can be assessed by electrophysiological assays testing for sodium channel activity. One aspect of the present invention is based on the use of the peptides described herein as sodium channel blockers. In one aspect of the present invention, it has been found that certain peptides show selectivity as $Na_v1.7$ sodium channel blockers. Based upon this property, these peptides are considered useful in treating or preventing pain.

More specifically, the present invention is directed to peptides that are blockers of sodium channels. In one embodiment, peptides having preferred sodium channel blocking properties exhibit an $IC_{50}$ of about 500 nM or less in one or more of the sodium electrophysiological assays described herein, or an $IC_{50}$ of about 100 nM or less, or an $IO_{50}$ of about 10 nM or less, or about 1 nM or less.

Peptides of the invention can be tested for their sodium channel blocking activity using electrophysiological assays known in the art (e.g., Clare et al., *Drug Discovery Today* 5: 506-520 (2000), such as the assays disclosed herein.

In Vitro Assay Protocols

FLIPR® Assays:

Recombinant $Na_v1.7$ Cell Line:

In vitro assays were performed in a recombinant cell line expressing cDNA encoding the α-subunit ($Na_v1.7$, SCN9A, PN1, NE) of human $Na_v1.7$ (Accession No. NM_002977). The cell line was provided by investigators at Yale University (Cummins et al., *J. Neurosci.* 18(23): 9607-9619 (1998)). For dominant selection of the $Na_v1.7$-expressing clones, the expression plasmid co-expressed the neomycin resistance gene. The cell line was constructed in the human embryonic kidney cell line, HEK293, under the influence of the CMV major late promoter, and stable clones were selected using limiting dilution cloning and antibiotic selection using the neomycin analogue, G418. Recombinant β- and γ-subunits were not introduced into this cell line. Additional cell lines expressing recombinant $Na_v1.7$ cloned from other species can also be used, alone or in combination with various β-subunits, γ-subunits or chaperones.

Non-Recombinant Cell Lines Expressing Native $Na_v1.7$:

Alternatively, in vitro assays can be performed in a cell line expressing native, non-recombinant $Na_v1.7$, such as the ND7 mouse neuroblastoma X rat dorsal root ganglion (DRG) hybrid cell line ND7/23, available from the European Cell Culture Collection (Cat. No. 92090903, Salisbury, Wiltshire, United Kingdom). The assays can also be performed in other cell lines expressing native, non-recombinant $Na_v1.7$ from various species, or in cultures of fresh or preserved sensory neurons, such as dorsal root ganglion (DRG) cells, isolated from various species. Primary screens or counter-screens of other voltage-gated sodium channels can also be performed, and the cell lines can be constructed using methods known in the art, purchased from collaborators or commercial establishments, and they can express either recombinant or native channels. The primary counter-screen is for one of the central neuronal sodium channels, $Na_v1.2$ (rBIIa), expressed in HEK293 host cells (Ilyin et al., *Br. J. Pharmacol.* 144: 801-812 (2005)). Pharmacological profiling for these counter-screens is carried out under conditions similar to the primary or alternative $Na_v1.7$ assays described below.

Cell Maintenance:

Unless otherwise noted, cell culture reagents were purchased from Mediatech of Herndon, Va. The recombinant $Na_v1.7$/HEK293 cells were routinely cultured in growth medium consisting of Dulbecco's minimum essential medium containing 10% fetal bovine serum (FBS, Hyclone, Thermo Fisher Scientific, Logan, Utah), 100 U/mL penicillin, 100 μg/mL streptomycin, 2-4 mM L-glutamine, and 500 mg/mL G418. For natural, non-recombinant cell lines, the selective antibiotic is omitted, and additional media formulations can be applied as needed.

Assay Buffer:

The assay buffer was formulated by removing 120 mL from a 1 L bottle of fresh, sterile $dH_2O$ (Mediatech, Herndon, Va.) and adding 100 mL of 10×HBSS that does not contain $Ca^{++}$ or $Mg^{++}$ (Gibco, Invitrogen, Grand Island, N.Y.) followed by 20 mL of 1.0 M Hepes, pH 7.3 (Fisher Scientific, BP299-100). The final buffer consisted of 20 mM Hepes, pH 7.3, 1.261 mM $CaCl_2$, 0.493 mM $MgCl_2$, 0.407 mM $Mg(SO)_4$, 5.33 mM KCl, 0.441 mM $KH_2PO_4$, 137 mM NaCl, 0.336 mM $Na_2HPO4$ and 0.556 mM D-glucose (Hanks et al., *Proc. Soc. Exp. Biol. Med.* 71:196 (1949)), and the simple formulation was typically the basic buffer throughout the assay (i.e., all wash and addition steps).

CoroNa™ Green AM $Na^+$ Dye for Primary Fluorescence Assay:

The fluorescence indicator used in the primary fluorescence assay was the cell permeant version of CoroNa™ Green (Invitrogen, Molecular Probes, Eugene, Oreg.), a dye that emits light in the fluorescence range (Harootunian et al., *J. Biol. Chem.* 264(32):19458-19467 (1989)). The intensity of this emission, but not the wavelength range, is increased when the dye is exposed to $Na^+$ ions, to which it can bind with partial selectivity. Cells expressing $Na_v1.7$ or other sodium channels were loaded with the CoroNa™ Green dye immediately in advance of the fluorescence assay, and then, after agonist stimulation, the mobilization of $Na^+$ ions was detected as the $Na^+$ ions flowed from the extracellular fluid into the cytoplasm through the activated sodium channel pores. The dye was stored in the dark as a lyophilized powder, and then an aliquot was dissolved immediately before the cell loading procedure, according to the instructions of the manufacturer to a stock concentration of 10 mM in DMSO. It was then diluted in the assay buffer to a 4× concentrated working solution, so that the final concentration of the dye in the cell loading buffer was 5 μM.

Membrane Potential Dye for Alternative Fluorescence Assays:

A fluorescence indicator that can be used in alternative fluorescence assays is the blue version membrane potential dye (MDS, Molecular Devices, Sunnyvale, Calif.), a dye that detects changes in molecules following a change in membrane potential. An increase in fluorescence is expected if agonist stimulation provokes a change in membrane potential. Cells expressing $Na_v1.7$ or other sodium channels are incubated with the membrane potential dye 30-60 minutes before the fluorescence assay. In the case of the KCl pre-stimulation version of the assay, the dye and all other components are washed out immediately before the assay, and the dye is then replaced. In the version absent of KCl pre-stimulation, the dye remains on the cells and is not washed out or replaced. The dye is stored in the dark as a lyophilized powder, and then an aliquot is dissolved in assay buffer to form a 20×-concentrated stock solution that can be used for several weeks.

Agonists:

In the fluorescence assays, two agonists were used in combination, namely 1) veratridine, and 2) the venom from the yellow scorpion, *Leiurus quinquestriatus hebraeus*. Veratridine is an alkaloid small molecule that facilitates the capture of channel openings by inhibiting inactivation, and the scorpion venom is a natural preparation that includes peptide toxins selective for different subsets of voltage-gated sodium channels. These scorpion toxins inhibit the fast inactivation of their cognate target channels. Stock solutions of the agonists were prepared to 40 mM in DMSO (veratridine) and 1 mg/mL in $dH_2O$ (scorpion venom), and then diluted to make a 4× or 2× stock (depending on the particular assay) in assay buffer, the final concentration being 100 μM (veratridine) and 10 μg/mL (scorpion venom). Both of the agonists were purchased from Sigma Aldrich, St. Louis, Mo.

Test Compounds:

Test compounds were dissolved in DMSO to yield 10 mM stock solutions. The stock solutions were further diluted using DMSO in 1:3 serial dilution steps with 10 points (10,000 μM, 3,333 μM, 1,111 μM, 370 μM, 123 μM, 41 μM, 14 μM, 4.6 μM, 1.5 μM and 0.5 μM). The stock solutions were further diluted in assay buffer (1:125) as 4× stock serial dilutions with a DMSO concentration of 0.8% (final DMSO, in the assay, from the compounds component=0.2%), so that the final concentrations of the compounds in the assay were 20 μM, 6.7 μM, 2.2 μM, 0.74 μM, 0.25 μM, 0.08 μM, 0.03 μM, 0.01 μM, 0.003 μM and 0.001 μM. If a particular test article appeared to be especially potent, then the concentration curve was adjusted, e.g., to 10-fold lower concentrations, in order to perform the dose-response in a more relevant concentration range. Compound dilutions were added during the dye-loading and pre-stimulation step, and then again during the fluorescence assay, early in the kinetic read. Compound dilutions were added in duplicate rows across the middle 80 wells of the 96-well plate, whereas the fully stimulated and the fully inhibited controls (positive and negative) were located in the top 4 side wells and the bottom 4 side wells, respectively, on the left and right sides of the assay plate.

Data Analysis:

The data were analyzed according to methods known in the art or using the GraphPad® Prism Version 4.0 or higher Program (available from GraphPad Software, San Diego, Calif.) to determine the $IC_{50}$ value for the test article. At least one standard reference compound was evaluated during each experiment.

FLIPR® or FLIPR$^{TETRA}$® Sodium Dye Assay with KCl and Test Article Pre-Incubation:

Cells were prepared by plating the recombinant HEK293 cells or other host cells expressing either recombinant or non-recombinant, native $Na_v1.7$ α-subunit, alone or in combination with various β- and γ-subunits at a density of ~40,000 cells/well into a 96-well black, clear-bottom, PDL-coated plate. The assay can be adapted to 384-well or 1,536-well format, if desired, using proportionately fewer cells and less media. The plate was then incubated in growth media, with or without selective antibiotic, overnight at 37° C. at 5% $CO_2$, 95% humidity, in preparation for the assay. For counter-screens of other voltage-gated sodium channels, the procedure was similar, though optimal densities of cells, media and subsequent assay components can be fine-tuned for the particular cell line or isoform.

The next day, at the start of the assay, the media was flicked from the cells and the wells were washed once with 50 μL/well assay buffer (1× Hank's balanced salt solution without sodium bicarbonate or phenol red, 20 mM Hepes, pH 7.3) and then pre-incubated with the test articles, CoroNa™ Green AM sodium dye (for cell loading) and KCl for re-polarization and synchronization of the channels in the entire population of cells. For this dye-loading and pre-stimulation step, the following components were added immediately after the wash step: 1) the compound dilutions and controls were added as 4× concentrates in assay buffer at 50 μL/well; 2) CoroNa™ Green AM dye was diluted from the stock solution to 20 μM in assay buffer (4× concentrate) and added to the plate at 50 μL/well; and 3) a solution of 180 mM KCl (2×) was prepared by diluting a 2 M stock solution into assay buffer and the solution was added to the cells at 100 μL/well. The cells were incubated at 25° C. in the dark for 30 min. before their fluorescence was measured.

The plates containing dye-loaded cells were then flicked to remove the pre-incubation components and washed once with 100 μL/well assay buffer. A 100 μL/well aliquot of assay buffer was added back to the plate, and the real-time assay was commenced. The fluorescence of cells was measured using a fluorescence plate reader (FLIPR$^{TETRA}$® or FLIPR384®, MDS, Molecular Devices, Sunnyvale, Calif.). Samples were excited by either a laser or a PMT light source (Excitation wavelength=470-495 nM) and the emissions were filtered (Emission wavelength=515–575 nM). The additions of test compound and the channel activators in this cell-based, medium-to-high throughput assay were performed on the fluorescence plate reader. The results (expressed as relative fluorescence units) were captured by means of camera shots every 1-3 seconds, then displayed in real-time and stored. Generally, there was a 15 second base line, with camera shots taken every 1.5 second, then the test compounds were added, then another 120 seconds baseline was conducted, with camera shots taken every 3 seconds; and finally, the agonist solution (containing veratridine and scorpion venom) was added. The amplitude of fluorescence increase, resulting from the binding of $Na^+$ ions to the CoroNa™ Green dye, was captured for about 180 seconds thereafter. Results were expressed in relative fluorescence units (RFU) and were determined by using the maximum signal during the latter part of the stimulation; or the maximum minus the minimum during the whole agonist stimulation period; or by taking the area under the curve for the whole stimulation period.

The assay can be performed as a screening assay as well as with the test articles present in standard amounts (e.g., 10 μM) in only one or two wells of a multi-well plate during the primary screen. Hits in this screen are typically profiled more exhaustively (multiple times), subjected to dose-response or competition assays and tested in counter screens against other voltage-gate sodium channels or other biologically relevant target molecules.

FLIPR® or FLIPR$^{TETRA}$® Membrane Potential Assay with KCl and Test Article Pre-Incubation:

Cells are prepared by plating the recombinant HEK293 cells or other host cells expressing either recombinant or non-recombinant, native $Na_v1.7$ α-subunit, alone or in combination with various β- and γ-subunits at a density of about 40,000 cells/well into a 96-well black, clear-bottom, PDL-coated plate. The assay can be adapted to 384-well or 1,536-well format, if desired, using proportionately fewer cells and less media. The plate is then incubated in growth media, with or without selective antibiotic, overnight at 37° C. at 5% $CO_2$, 95% humidity, in preparation for the assay (see, e.g., Benjamin et. al., *J. Biomol. Screen* 10(4):365-373 (2005)). For screens and counter-screens of other voltage-gated sodium channels, the assay protocol is similar, though optimal densities of cells, media and subsequent assay components can be fine-tuned for the particular cell line or sodium channel isoform being tested.

The next day, at the start of the assay, the media is flicked from the cells and the wells are washed once with 50 μL/well assay buffer (1× Hank's balanced salt solution without sodium bicarbonate or phenol red, 20 mM Hepes, pH 7.3) and then pre-incubated with the test articles, the membrane potential dye (for cell loading), and the KCl for re-polarization and synchronization of the channels in the entire population of cells. For this dye-loading and pre-stimulation step, the following components are added immediately after the wash step: 1) the compound dilutions and controls are added as 4× concentrates in assay buffer at 50 μL/well; 2) membrane potential dye is diluted from the stock solution in assay buffer (4× concentrate) and added to the plate at 50 μL/well; and 3) a solution of 180 mM KCl (2×) is prepared by diluting a 2 M stock solution into assay buffer and the solution added to the cells at 100 μL/well. The cells are incubated at 37° C. in the dark for 30-60 minutes before their fluorescence is measured.

The plates containing dye-loaded cells are then flicked to remove the pre-incubation components and washed once with 50 μL/well assay buffer. A 50 μL/well aliquot of membrane potential dye is added back to the plate, and the real-time assay is commenced. The fluorescence of cells is measured using a fluorescence plate reader (FLIPR$^{TETRA}$® or FLIPR384®, MDS, Molecular Devices, Sunnyvale, Calif.). Samples are excited by either a laser or a PMT light source (Excitation wavelength –510-545 nM) and the emissions are filtered (Emission wavelength=565–625 nM). The additions of the compounds (first) and then the channel activators (later) in this are performed on the fluorescence plate reader and the results, expressed as relative fluorescence units (RFU), are captured by means of camera shots every 1-3 seconds, then displayed in real-time and stored. Generally, there is a 15 seconds base line, with camera shots taken every 1.5 seconds, then the test compounds are added, then another 120 seconds baseline is conducted, with camera shots taken every 3 seconds. Finally, the agonist solution (containing veratridine and scorpion venom) is added. The amplitude of fluorescence increase, resulting from the detection of membrane potential change, is captured for about 120 seconds thereafter. Results are expressed in relative fluorescence units (RFU) and can be determined by using the maximum signal during the latter part of the stimulation; or the maximum minus the minimum during the whole stimulation period; or by taking the area under the curve for the whole stimulation period.

The assay can be performed as a screening assay as well with the test articles present in standard amounts (e.g., 10 μM) in only one or two wells of a multi-well plate during the primary screen. Hits in this screen are typically profiled more exhaustively (multiple times), subjected to dose-response or competition assays and tested in counter screens against other voltage-gate sodium channels or other biologically relevant target molecules.

FLIPR® or FLIPR$^{TETRA}$® Sodium Dye Assay without KCl and Test Article Pre-Incubation:

Cells are prepared by plating the recombinant HEK293 cells or other host cells expressing either recombinant or non-recombinant, native, $Na_v1.7$ α-subunit, alone or in combination with various β- and γ-subunits at a density of about 40,000 cells/well into a 96-well black, clear-bottom, PDL-coated plate. The assay can be adapted to 384-well or 1,536-well format, if desired, using proportionately fewer cells and less media. The plate is then incubated in growth media, with or without selective antibiotic, overnight at 37° C. at 5% $CO_2$, 95% humidity, in preparation for the assay. For counter screens of other voltage-gated sodium channels, the procedure is similar, though optimal densities of cells, media and subsequent assay components can be fine-tuned for the particular cell line or isoform.

The next day, at the start of the assay, the media is flicked from the cells and the wells washed once with 50 μL/well assay buffer (1× Hank's balanced salt solution without sodium bicarbonate or phenol red, 20 mM Hepes, pH 7.3). Membrane potential dye is then added to each well of the 96-well plate (50 μL/well), from a freshly diluted sample of the stock (now at 4× concentration) in the assay buffer. The cells are incubated at 37° C. in the dark for 30-60 minutes before their fluorescence is measured.

In this standard membrane potential assay, the 96-well plate containing dye-loaded cells is then loaded directly onto the plate reader without aspirating the dye solution and without any further washing of the cells. The fluorescence of cells is measured using a fluorescence plate reader (FLIPR$^{TETRA}$® or FLIPR384®, MDS, Molecular Devices, Sunnyvale, Calif.). Samples are excited by either a laser or a PMT light source (Excitation wavelength=510–545 nM) and the emissions are filtered (Emission wavelength=565–625 nM). The additions of the test compounds (first, 50 μL/well from a 4× stock plate) and then the channel activators (later, 100 μL/well from a 2× stock solution) in this kinetic assay are performed on the fluorescence plate reader. The results, expressed as relative fluorescence units (RFU), are captured by means of camera shots every 1-3 seconds, then displayed in real-time and stored. Generally, there is a 15 sec. base line, with camera shots taken every 1.5 sec., then the test compounds are added, then another 120 sec. baseline is conducted, with camera shots taken every 3 sec. Finally, the agonist solution (containing veratridine and scorpion venom) is added. The amplitude of fluorescence increase, resulting from the detection of membrane potential change, is captured for ~120 sec. thereafter. Results are expressed in relative fluorescence units (RFU) and can be determined by using the maximum signal during the latter part of the stimulation; or the maximum minus the minimum during the whole stimulation period or by taking the area under the curve for the whole stimulation period.

The assay can be performed as a screening assay as well, with the test articles present in standard amounts (e.g. 10 μM) in only one or two wells of a multi-well plate during the primary screen. Hits in this screen are typically profiled more exhaustively (multiple times), subjected to dose-response or competition assays and tested in counter screens against other voltage-gate sodium channels or other biologically relevant target molecules.

Electrophysiology Assay

Cells:
The $hNa_v1.7$ expressing HEK-293 cells were plated on 35 mm culture dishes pre-coated with poly-D-lysine in standard DMEM culture media (Mediatech, Inc., Herndon, Va.) and incubated in a 5% $CO_2$ incubator at 37° C. Cultured cells were used approximately 12-48 hours after plating.

Electrophysiology:
On the day of experimentation, the 35 mm dish was placed on the stage of an inverted microscope equipped with a perfusion system that continuously perfused the culture dish with fresh recording media. A gravity driven superfusion system was used to apply test solutions directly to the cell under evaluation. This system consisted of an array of glass pipettes connected to a motorized horizontal translator. The outlet of the shooter was positioned approximately 100 μm from the cell of interest.

Whole cell currents were recorded using the whole-cell patch clamp configuration using an Axopatch 200B amplifier (Axon Instruments, Foster City Calif.), 1322A A/D converter (Axon Instruments) and pClamp software (v. 8; Axon Instruments) and stored on a personal computer. Gigaseals were formed and the whole-cell configuration was established in voltage clamp mode, and membrane currents generated by $hNa_v1.7$ were recorded in gap free mode. Borosilicate glass pipettes having resistance values between 1.5 and 2.0 MΩ when filled with pipette solution and series resistance (<5 MΩ) were compensated 75-80%. Signals were sampled at 50 kHz and low pass filtered at 3 kHz.

The voltage clamp protocol to examine $hNa_v1.7$ currents was as follows. First, the standard current-voltage relationship was tested by pulsing the cell from the holding voltage ($V_h$) of −120 mV by a series of 5 msec long square-shaped test pulses incrementing in +10 mV steps over the membrane voltage range of −90 mV to +60 mV at the pace of stimulation of 0.5 Hz. This procedure determined the voltage that elicited the maximal current ($V_{max}$). Second, $V_h$ was re-set to −120 mV and a steady-state inactivation (SSIN) curve was taken by the standard double-pulse protocol: 100 ms depolarizing pre-pulse was incremented in steps of +10 mV (voltage range from −90 mV to 0 mV) immediately followed by the 5 ms long test pulse to −10 mV at the pace of stimulation of 0.2 Hz. This procedure determined the voltage of full inactivation ($V_{full}$). Third, the cell was repeatedly stimulated with the following protocol, first in the absence of the test compound then in its presence. The protocol consisted of depolarizing the cell from the holding potential of −120 mV to the $V_{full}$ value for 4.5 seconds then repolarizing the cell to the holding potential for 10 ms before applying the test pulse to the $V_{max}$ for 5 ms. The amount of inhibition produced by the test compound was determined by comparing the current amplitude elicited by the test pulse in the absence and presence of the compound.

Solutions and Chemicals:

For electrophysiological recordings the external solution was either standard, DMEM supplemented with 10 mM HEPES (pH adjusted to 7.34 with NaOH and the osmolarity adjusted to 320) or Tyrodes salt solution (Sigma, USA) supplemented with 10 mM HEPES (pH adjusted to 7.4 with NaOH; osmolarity=320). The internal pipette solution contained (in mM): NaCl (10), CsF (140), $CaCl_2$ (1), $MgCl_2$ (5), EGTA (11), HEPES (10: pH 7.4, 305 mOsm). Compounds were prepared first as series of stock solutions in DMSO and then dissolved in external solution; DMSO content in final dilutions did not exceed 0.3%. At this concentration, DMSO does not affect sodium currents. Vehicle solution used to establish base line also contained 0.3% DMSO.

Data Analysis:

Data is analyzed off-line using Clampfit software (pClamp, v. 8; Axon Instruments) and graphed using Graph-Pad Prizm (v. 4.0 or higher) software.

In Vivo Assay for Pain

The peptides of the invention can be tested for their antinociceptive activity in the formalin model as described in Hunskaar et al., *J. Neurosci. Methods* 14: 69-76 (1985). Male Swiss Webster NIH mice (20-30 g; Harlan, San Diego, Calif.) can be used in all experiments. Food is withdrawn on the day of experiment. Mice are placed in Plexiglass jars for at least 1 hour to acclimate to the environment. Following the acclimation period, mice are weighed and given either the compound of interest administered i.p. or p.o., or the appropriate volume of vehicle (for example, 10% Tween-80 or 0.9% saline, and other pharmaceutically acceptable vehicles) as control. Fifteen minutes after the i.p. dosing, and 30 minutes after the p.o. dosing, mice are injected with formalin (20 μL of 5% formaldehyde solution in saline) into the dorsal surface of the right hind paw. Mice are transferred to the Plexiglass jars and monitored for the amount of time spent licking or biting the injected paw. Periods of licking and biting are recorded in 5-minute intervals for 1 hour after the formalin injection. All experiments are done in a blinded manner during the light cycle. The early phase of the formalin response is measured as licking/biting between 0-5 minutes, and the late phase is measured from 15-50 minutes. Differences between vehicle and drug treated groups can be analyzed by one-way analysis of variance (ANOVA). A P value <0.05 is considered significant. A compound is considered to be efficacious for treating acute and chronic pain if it has activity in blocking both the early and second phase of formalin-induced paw-licking activity.

In Vivo Assays for Inflammatory or Neuropathic Pain

Test Animals:

Each experiment uses rats weighing between 200-260 grams at the start of the experiment. The rats are group-housed and have free access to food and water at all times, except prior to oral administration of a test compound when food is removed for 16 hours before dosing. A control group acts as a comparison to rats treated with test compound. The control group is administered the carrier as used for the test compound. The volume of carrier administered to the control group is the same as the volume of carrier and test compound administered to the test group.

Inflammatory Pain:

To assess the actions of test compound on the treatment of inflammatory pain, the Freund's complete adjuvant ("FCA") model of inflammatory pain is used. FCA-induced inflammation of the rat hind paw is associated with the development of persistent inflammatory mechanical and thermal hyperalgesia and provides reliable prediction of the anti-hyperalgesic action of clinically useful analgesic drugs (Bartho et al., *Naunyn-Schmiedeberg's Archives of Pharmacol.* 342:666-670 (1990)). The left hind paw of each animal is administered a 50 μL intraplantar injection of 50% FCA. 24-hour post-injection, each animal is assessed for response to noxious mechanical stimuli by determining the paw withdrawal threshold (PWT), or to noxious thermal stimuli by determining the paw withdrawal latency (PWL), as described below. Rats are then administered a single injection of either a test compound or 30 mg/kg of a positive control compound (e.g., indomethacin). Responses to noxious mechanical or thermal stimuli are then determined 1, 3, 5 and 24 hours post administration. Percentage reversal of hyperalgesia for each animal is defined as:

$$\% \text{ reversal} = \frac{[(\text{post administration } PWT \text{ or } PWL) - (\text{pre-administration } PWT \text{ or } PWL)]}{[(\text{baseline } PWT \text{ or } PWL) - (\text{pre-administration } PWT \text{ or } PWL)]} \times 100$$

Neuropathic Pain:

To assess the actions of the test compound for the treatment of neuropathic pain the Seltzer model or the Chung model can be used.

In the Seltzer model, the partial sciatic nerve ligation model of neuropathic pain is used to produce neuropathic hyperalgesia in rats (Seltzer et al., *Pain* 43:205-218 (1990)). Partial ligation of the left sciatic nerve is performed under isoflurane/$O_2$ inhalation anaesthesia. Following induction of anaesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anaesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after drug administration. Percentage reversal of neuropathic hyperalgesia is defined as:

$$\% \text{ reversal} = \frac{[(\text{post administration } PWT) - (\text{pre-administration } PWT)]}{[(\text{baseline } PWT) - (\text{pre-administration } PWT)]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia, a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is (are) isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is (are) not manipulated. Following surgery, animals are weighed, administered a subcutaneous (s.c.) injection of saline or ringers lactate, the wound area is dusted with antibiotic powder and they are kept on a warm pad until they recover from the anaesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a test compound. The animals can also be assessed for response to noxious thermal stimuli or for tactile allodynia, as described below. The Chung model for neuropathic pain is described in Kim et al., *Pain* 50(3):355-363 (1992).

Tactile Allodynia:

Sensitivity to non-noxious mechanical stimuli can be measured in animals to assess tactile allodynia. Rats are transferred to an elevated testing cage with a wire mesh floor and allowed to acclimate for a period of 15 minutes. After habituation, a series of von Frey monofilaments are applied to the plantar surface of the affected (ipsilateral) hindpaw to determine the animal's withdrawal threshold. The first filament used possesses a buckling weight of 9.1 grams (0.96 log value) and is applied up to five times to see if it elicits a withdrawal response. If the animal has a withdrawal response, then the next lightest filament in the series would be applied up to five times to determine if it also could elicit a response. This procedure is repeated with subsequent lesser filaments until there is no response and the identity of the lightest filament that elicits a response is recorded. If the animal does not have a withdrawal response from the initial 9.1 grams filament, then subsequent filaments of increased weight are applied until a filament elicits a response and the identity of this filament is recorded. For each animal, three measurements are made at every time point to produce an average withdrawal threshold determination. Tests can be performed prior to, and at 1, 2, 4 and 24 hours post drug administration. Flinching, paw withdrawal or licking of the paw are considered nociceptive behavioral responses.

Mechanical Hyperalgesia:

Sensitivity to noxious mechanical stimuli can be measured in animals using the paw pressure test to assess mechanical hyperalgesia. In rats, hind paw withdrawal thresholds ("PWT"), measured in grams, in response to a noxious mechanical stimulus are determined using an analgesymeter (Model 7200, commercially available from Ugo Basile of Italy), as described in Stein et al., *Biochemistry & Behavior* 31:451-455 (1988). The rat's paw is placed on a small platform, and weight is applied in a graded manner up to a maximum of 250 grams. The endpoint is taken as the weight at which the paw is completely withdrawn. PWT is determined once for each rat at each time point. PWT can be measured only in the injured paw, or in both injured and non-injured paws. In one non-limiting embodiment, mechanical hyperalgesia associated with nerve injury induced pain (neuropathic pain) can be assessed in rats. Rats are tested prior to surgery to determine a baseline, or normal, PWT. Rats are tested again 2 to 3 weeks post-surgery, prior to, and at different times after (e.g., 1, 3, 5 and 24 hours) drug administration. An increase in PWT following drug administration indicates that the test compound reduces mechanical hyperalgesia.

Thermal Hyperalgesia:

The plantar test can be used to assess thermal hyperalgesia. For this test, hind paw withdrawal latencies to a noxious thermal stimulus are determined using a plantar test apparatus (commercially available from Ugo Basile of Italy) following the technique described by K. Hargreaves et al., "A New and Sensitive Method for Measuring Thermal Nociception in Cutaneous Hyperalgesia," *Pain* 32(1):77=88 (1988). The maximum exposure time is set at 32 seconds to avoid tissue damage and any directed paw withdrawal from the heat source is taken as the end point. Three latencies are determined at each time point and averaged. Only the affected (ipsilateral) paw is tested.

Pharmaceutical Compositions

Although a C-terminal modified Protoxin II peptide of formula (I), a pharmaceutically acceptable salt, prodrug or solvate of the invention may be administered to a subject in the form of a raw chemical without any other components present, the peptide is preferably administered as part of a pharmaceutical composition containing the peptide combined with a suitable pharmaceutically acceptable carrier.

Pharmaceutical compositions within the scope of the present invention include all compositions where a C-terminal modified Protoxin II peptide of formula (I), a pharmaceutically acceptable salt, prodrug or solvate of the invention is combined with a pharmaceutically acceptable carrier. In a preferred embodiment, the peptide is present in the composition in an amount that is effective to achieve its intended therapeutic purpose. While individual subject needs may vary, a determination of optimal ranges of effective amounts of each peptide is within the skill of the art. Typically, the peptides may be administered to a subject, e.g., a human, at a dosage of about 0.01, 0.05, 0.1, 0.5, 1, 5, 10, 50, 100, or 500 μg/kg body weight, depending on the specific peptide selected, the desired therapeutic response, the route of administration, the formulation, the medical condition of the subject, and other factors known to those of skill in the art.

A pharmaceutical composition of the present invention is preferably manufactured in a manner which itself will be known in view of the instant disclosure, for example, by means of conventional mixing, dissolving, formulating or lyophilizing processes.

A pharmaceutical composition of the present invention can contain from about 0.01 to 99 percent by weight, and preferably from about 0.25 to 75 percent by weight, of at least one C-terminal modified Protoxin II peptide of formula (I), a pharmaceutically acceptable salt, prodrug or solvate.

A method of the present invention, such as a method for treating a disorder or providing preemptive or palliative treatment of a disorder responsive to the blockade of sodium channels in a subject in need thereof, can further comprise administering a second therapeutic agent to the subject in combination with a C-terminal modified Protoxin II peptide of formula (I), a pharmaceutically acceptable salt, prodrug or solvate of the present invention. The other therapeutic agents are preferably administered in an effective amount.

Effective amounts of the other therapeutic agents will generally be known to or readily ascertainable by those skilled in the art. It is well within the skilled artisan's purview to determine the other therapeutic agents' optimal effective-amount range.

A C-terminal modified Protoxin H peptide of formula (I), a pharmaceutically acceptable salt, prodrug or solvate of the invention (i.e., the first therapeutic agent) and the second therapeutic agent can act additively or synergistically. Alternatively, the second therapeutic agent can be used to treat a disorder or condition that is same or different from the disorder or condition for which the first therapeutic agent is being administered.

In one embodiment, a C-terminal modified Protoxin II peptide of formula (I), a pharmaceutically acceptable salt, prodrug or solvate of the invention is administered simultaneously or concurrently with the second therapeutic agent; for example, in a single composition comprising both an effective amount of a peptide of the invention, and an effective amount of the second therapeutic agent. Accordingly, the present invention further provides a pharmaceutical composition comprising a combination of a peptide of the invention, the second therapeutic agent, and a pharmaceutically acceptable carrier. Alternatively, a C-terminal modified Protoxin II peptide of formula (I), a pharmaceutically acceptable salt, prodrug or solvate of the invention is administered simultaneously or concurrently with the second therapeutic agent, for example, in separate compositions, wherein a first pharmaceutical composition comprising an effective amount of a peptide of the invention and a second pharmaceutical composition comprising an effective amount of the second therapeutic agent. In another embodiment, an effective amount of a peptide of the invention is administered prior, or subsequent to administration of an effective amount of the second therapeutic agent.

The second therapeutic agent can be an opioid agonist, a non-opioid analgesic, a non-steroidal anti-inflammatory agent, an antimigraine agent, a Cox-II inhibitor, a β-adrenergic blocker, an anticonvulsant, an antidepressant, an anticancer agent, an agent for treating addictive disorder, an agent for treating Parkinson's disease and parkinsonism, an agent for treating anxiety, an agent for treating epilepsy, an agent for treating a seizure, an agent for treating a stroke, an agent for treating a pruritic condition, an agent for treating psychosis, an agent for treating ALS, an agent for treating a cognitive disorder, an agent for treating a migraine, an agent for treating vomiting, an agent for treating dyskinesia, or an agent for treating depression, or a mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

Examples of useful non-opioid analgesics include non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Examples of other suitable non-opioid analgesics include the following, non limiting, chemical classes of analgesic, antipyretic, nonsteroidal antiinflammatory drugs: salicylic acid derivatives, including aspirin, sodium salicylate, choline magnesium trisalicylate, salsalate, diflunisal, salicylsalicylic acid, sulfasalazine, and olsalazin; para aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, *Analgesic Antipyretic and Antiinflammatory Agents and Drugs Employed in the Treatment of Gout*, in Goodman & Gilman's *The Pharmacological Basis of Therapeutics* 617-57 (Perry B. Molinhoff and Raymond W. Ruddon eds., 9th ed 1996) and Glen R. Hanson, *Analgesic, Antipyretic and Anti Inflammatory Drugs* in Remington: *The Science and Practice of Pharmacy* Vol. II 1196-1221 (A. R. Gennaro ed. 19th ed. 1995) which are hereby incorporated by reference in their entireties. Suitable Cox-II inhibitors and 5-lipoxygenase inhibitors, as well as combinations thereof, are described in U.S. Pat. No. 6,136,839, which is hereby incorporated by reference in its entirety. Examples of useful Cox II inhibitors include, but are not limited to, rofecoxib and celecoxib.

Examples of useful antimigraine agents include, but are not limited to, alpipride, bromocriptine, dihydroergotamine, dolasetron, ergocornine, ergocorninine, ergocryptine, ergonovine, ergot, ergotamine, flumedroxone acetate, foriazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenyl-hydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, *solanum*, strontium bromide, suclofenide, sulthiame, tetrantoin, tiagabine, topiramate, trimethadione, valproic acid, valpromide, vigabatrin, and zonisamide.

Examples of useful therapeutic agents for treating depression include, but are not limited to, tricyclic antidepressants such as amitryptyline, amoxapine, bupropion, clomipramine, desipramine, doxepin, imipramine, maprotiline, nefazadone, nortriptyline, protriptyline, trazodone, trimipramine, and venlafaxine; selective serotonin reuptake inhibitors such as citalopram, (S)-citalopram, fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate. Other examples of useful antidepressants include, but are not limited to, binedaline, caroxazone, dimethazan, fencamine, indalpine, indeloxazine hydrocholoride, nefopam, nomifensine, oxitriptan, oxypertine, thiazesim, benmoxine, iproclozide, iproniazid, nialamide, octamoxin, cotinine, rolicyprine, rolipram, metralindole, mianserin, mirtazepine, adinazolam, amitriptyline, amitriptylinoxide, butriptyline, demexiptiline, dibenzepin, dimetacrine, dothiepin, fluacizine, imipramine N-oxide, iprindole, lofepramine, melitracen, metapramine, noxiptilin, opipramol, pizotyline, propizepine, quinupramine, tianeptine, adrafinil, benactyzine, butacetin, dioxadrol, duloxetine, etoperidone, febarbamate, femoxetine, fenpentadiol, hematoporphyrin, hypericin, levophacetoperane, medifoxamine, milnacipran, minaprine, moclobemide, oxaflozane, piberaline, prolintane, pyrisuccideanol, ritanserin, roxindole, rubidium chloride, sulpiride, tandospirone, thozalinone, tofenacin, toloxatone, L-tryptophan, viloxazine, and zimeldine.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, and cisplatin.

Therapeutic agents useful for treating an addictive disorder include, but are not limited to, methadone, desipramine, amantadine, fluoxetine, buprenorphine, an opiate agonist, 3-phenoxypyridine, or a serotonin antagonist.

Examples of useful therapeutic agents for treating Parkinson's disease and parkinsonism include, but are not limited to, carbidopa/levodopa, pergolide, bromocriptine, ropinirole, pramipexole, entacapone, tolcapone, selegiline, amantadine, and trihexyphenidyl hydrochloride.

Examples of useful therapeutic agents for treating anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating epilepsy or seizure include, but are not limited to, carbamazepine, ethosuximide, gabapentin, lamotrigine, phenobarbital, phenytoin, primidone, valproic acid, trimethadione, benzodiazepines, gamma-vinyl GABA, acetazolamide, and felbamate.

Examples of useful therapeutic agents for treating a pruritic condition include, but are not limited to, naltrexone; nalmefene; danazol; tricyclics such as amitriptyline, imipramine, and doxepin; antidepressants such as those given below; menthol; camphor; phenol; pramoxine; capsaicin; tar; steroids; and antihistamines.

Examples of useful therapeutic agents for treating psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; and ziprasidone.

Examples of useful therapeutic agents for treating cognitive disorders include, but are not limited to, agents for treating dementia such as tacrine; donepezil; ibuprofen; antipsychotic drugs such as thioridazine and haloperidol; and antidepressant drugs such as those given below.

Examples of useful therapeutic agents for treating a migraine include, but are not limited to, sumatriptan; methysergide; ergotamine; caffeine; and beta-blockers such as propranolol, verapamil, and divalproex.

Examples of useful therapeutic agents for treating vomiting include, but are not limited to, 5-HT3 receptor antagonists such as ondansetron, dolasetron, granisetron, and tropisetron; dopamine receptor antagonists such as prochlorperazine, thiethylperazine, chlorpromazine, metoclopramide, and domperidone; glucocorticoids such as dexamethasone; and benzodiazepines such as lorazepam and alprazolam.

Examples of useful therapeutic agents for treating dyskinesia include, but are not limited to, reserpine and tetrabenazine.

The following examples are illustrative, but not limiting, of the C-terminal modified Protoxin II peptides of formula (I), pharmaceutically acceptable salts, prodrugs or solvates, compositions and methods of the present invention. Suitable modifications and adaptations of the variety of conditions and parameters normally encountered in clinical therapy and which are obvious to those skilled in the art in view of this disclosure are within the spirit and scope of the invention.

EXAMPLE 1

Synthesis of Orthogonally Protected Linear Protoxin II

Orthogonally protected linear Protoxin II was obtained by the solid-phase technique (see "Fmoc Solid Phase Peptide Synthesis; A Practical Approach," W. C. Chan (ed) and P. D. White (ed), Oxford University Press, 2000) using Pioneer peptide synthesizer. Fmoc-L-amino acids were purchased from Protein Technologies, Inc. H-amino acid-2-cl-Trt resin was purchased from AnaSpec Inc. HATU was purchased from Genscript Corp. Boc-Tyr(tBu)-OH, HPLC-graded solvents and ReagentPlus®-graded reagents were purchased from Sigma-Aldrich.

Peptides were assembled stepwise on 0.05 mmol of H-Trp(Boc)-2-Cl-Trt resin (0.42 mmol/g) using 8 fold excess of Fmoc amino acids. Fmoc protecting group was removed using 20% piperidine in DMF and free amine was coupled with amino acids/HATU/2,4,6-collidine. The side-chain protecting groups used for trifunctional residues were: trityl for Cys, His, Asn and Gln; t-butyl for Asp, Glu, Ser, Thr and Tyr; 2,2,4,6,7-pentamethyldihydrobenzofuran-5-sulfonyl for Arg; and t-butyloxycarbonyl for Lys and Trp.

Peptide on the resin was treated with acetic acid:trifluoroethanol:DCM (1:1:8) for 30 minutes at room temperature to cleave orthogonally protected peptide from the resin. The mixture was filtered and the filtrate was concentrated. Cold diethyl ether was added to precipitate peptides out and peptides were washed with diethyl ether for 3 times to obtain crude orthogonally protected peptide.

EXAMPLE 2

Synthesis of C-Terminal Modified Protoxin II Peptide

Several C-terminal modified Protoxin II peptides set forth in Table 3 were synthesized. The mixture of crude orthogonally protected peptide obtained from EXAMPLE 1 (0.13 g, 18 µmol, 1.0 eq.), HATU (67 mg, 176 mol, 10 eq.) and collidine (47 µL, 352 µmol, 20 eq.) in DMF (10 mL) was stirred for 10 min. A derivatizing agent $R_1NH_2$ or $R_1OH$ (176 µmol, 10 eq.), wherein $R_1$ is defined above, was added to the mixture and stirred for 3 hours. DMF was removed to get an oil.

TFA:TIS:3,6-Dioxa-1,8-octanedithiol:thioanisole:phenol:$H_2O$ (81.5:1:2.5:5:5:5 by volume) was added to the oil and stirred for 2 hours at room temperature. Deprotected peptide was treated with cold diethyl ether to precipitate peptides out and precipitated peptides were washed with diethyl ether 3 times. Crude linear peptides were purified by reversed Prep-HPLC and white solids were obtained.

Purified linear peptide solution in water (1 mg/10 mL) was added to 0.1 M of Tris/HCl buffer, 2.0 M of urea, 0.15 mM of glutathione ("GSH"), 0.3 mM of glutathione disulfide ("GSSG") solution that has a pH adjusted to pH 8 with saturated aqueous $NaHCO_3$. The reaction mixture was stirred overnight. Upon completion of the reaction, the reaction mixture was adjusted to pH 3 and purified by reversed Prep-HPLC (C18, 5 µm, 250 mm×21 mm, buffer; A: 0.1% v/v TFA in $H_2O$ and B: 0.1% v/v TFA in MeCN). Purified Protoxin II peptides were characterized by analytical LCMS (liquid chromatography-mass spectrometry) and NMR (nuclear magnetic resonance). Table 3 shows the LCMS data.

TABLE 3

| Protoxin II and C-Modified Protoxin II Peptide | SEQ ID NO: | C-terminal | LCMS Analysis Calc[2] | Obsd[3] |
|---|---|---|---|---|
| Protoxin II | 1 | —C(=O)OH | 3826.66 | 3826.8 $[M + 3H]^{3+}$ |
| Protoxin-$NH_2$ | 10 | —C(=O)$NH_2$ | 3825.68 | 3826.0 $[M + 4H]^{4+}$ |

TABLE 3-continued

LCMS Analysis

| Peptide | SEQ ID NO: | C-terminal | Calc[2] | Obsd[3] |
|---|---|---|---|---|
| Protoxin II-NHMe | 11 | –C(O)NHCH₃ | 3839.7 | 3840.8 [M + 4H]⁴⁺ |
| Protoxin II-OMe | 12 | –C(O)OCH₃ | 3840.69 | 3839.6 [M + 4H]⁴⁺ |
| Protoxin II-NHcyclohexyl | 13 | –C(O)NH-cyclohexyl | 3906.82 | 3906.8 [M + 4H]⁴⁺ |
| Protoxin II (D)-NHcyclohexyl[1] | 14 | –C(O)NH-cyclohexyl | 3906.82 | 3906.4 [M + 4H]⁴⁺ |
| Protoxin II-NHaniline | 15 | –C(O)NH-phenyl | 3901.78 | 3900.00 [M + 4H]⁴⁺ |
| Protoxin II-D-Trp | 16 | –C(O)NH-CH(CH₂-indolyl)-COOH | 4012.89 | 4011.8 [M + 4H]⁴⁺ |

[1] Stereochemistry of Trp₃₀ is D.
[2] Calc: calculated.
[3] Obsd: observed.

An example of the sequence of C-terminal modified Protoxin II peptide, Protoxin II-NHCH₃ (SEQ ID NO: 11), is shown below: YCQKWMWTCDSARKCCEGMVCRL-WCKKKLW-NHCH₃ (disulfide bridge C2-C16, C9-C21, C15-C25), or

YCQKWMWTCDSARKCCEGMVCRLWCKKKLW—NHCH₃

EXAMPLE 3

Sodium Channel Assays

Protoxin II and its C-terminal modified Protoxin II peptides set forth in Table 4 were assayed for sodium channel-blocking activity. As shown in Table 4, the peptides of the present invention are potent antagonists of the $Na_v1.7$ sodium channels. In addition, the peptides show selectivity as $Na_v1.7$ channel blockers, relative to $Na_v1.2$.

TABLE 4

Sodium Channel Blocking Activity

| Protoxin II and C-Modified Protoxin II Peptide | SEQ ID NO: | C-terminal | $Na_v1.7$ $IC_{50}$ (nM) FLIPR | EP | $Na_v1.2$ $IC_{50}$ (nM) FLIPR | EP |
|---|---|---|---|---|---|---|
| Protoxin II | 1 | –COOH | 59.7 (n = 3) | 1 | 379.3 (n = 3) | 100 |
| Protoxin-NH$_2$ | 10 | –C(O)NH$_2$ | ND[1] | 1 | ND | 8 |
| Protoxin II-NHMe | 11 | –C(O)NHMe | 64.3 (n = 3) | 0.042 | 992.7 (n = 3) | 3.48 |
| Protoxin II-OMe | 12 | –C(O)OMe | 8.4 | 0.6 ± 0.3 | 154.2 | 2.8 ± 0.8 |
| Protoxin II-NHcyclohexyl | 13 | –C(O)NH-cyclohexyl | 22 (n = 3) | ND | 282 (n = 3) | ND |
| Protoxin II (D)-NHcyclohexyl[2] | 14 | –C(O)NH-cyclohexyl | 31 (n = 3) | ND | 336 (n = 3) | ND |
| Protoxin II-NHaniline | 15 | –C(O)NH-phenyl | 5.1 (n = 3) | 0.8 ± 0.2 | 110.2 (n = 3) | 3.0 ± 0.5 |
| Protoxin II-D-Trp | 16 | –C(O)-NH-CH(CH$_2$-indolyl)-COOH (D-Trp) | 16.5 (n = 3) | ND | 101.6 (n = 3) | ND |

[1] ND: No data.
[2] Stereochemistry of Trp$_{30}$ is D.

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

Further preferred embodiments of the invention relate to:

1. A peptide having formula (I):

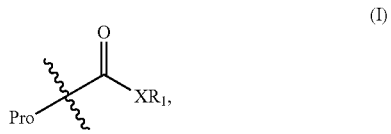

(I)

wherein:

Pro is Protoxin II having the amino acid sequence: $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Glu_{12}$-$Arg_{13}$-$Lys_{14}$-$Cys_{15}$-$Cys_{16}$-$Glu_{17}$-$Gly_{18}$-$Met_{19}$-$Val_{20}$-$Cys_{21}$-$Arg_{22}$-$Leu_{23}$-$Trp_{24}$-$Cys_{25}$-$Lys_{26}$-$Lys_{27}$-$Lys_{28}$-$Leu_{29}$-$Trp_{30}$ (SEQ ID NO: 1), wherein $Trp_{30}$ is D or L-$Trp_{30}$, X is —NH— or —O—, $R_1$ is $C_1$-$C_6$ alkyl, or $C_3$-$C_7$ cycloalkyl or $C_5$-$C_{10}$ aryl; or when X is —NH—, $R_1$ is —CH(R)—COOH, wherein R is selected from a group consisting of —H, $—CH_3$, $—CH_2CH_2CH_2—NH—C(NH_2)═NH$, $—CH_2CONH_2$, $—CH_2COOH$, $—CH_2CH_2COOH$, $—CH_2SH$, $—CH_2CH_2CONH_2$, $—CH(CH_3)CH_2CH_3$, $—CH_2CH(CH_3)_2$, $—CH(CH_3)_2$, $—CH_2CH_2CH_2NH_2$, $—CH_2CH_2SCH_3$, $—CH_2C_6H_6$, $—CH_2OH$, $—CH(OH)CH_3$,

,

, and or a pharmaceutically acceptable salt or solvate thereof.

2. The peptide according to 1, wherein said peptide is an isolated peptide.

3. The peptide according to 1 or 2, wherein $Trp_{30}$ is L-Trp.

4. The peptide according to 1 or 2, wherein $Trp_{30}$ is D-Trp.

5. The peptide according to any one of 1 to 4, wherein X is —NH—.

6. The peptide according to any one of 1 to 4, wherein X is —O—.

7. The peptide according to any one of 1 to 6, wherein $R_1$ is $C_1$-$C_4$ alkyl, preferably methyl, ethyl or propyl, and more preferably methyl.

8. The peptide according to any one of 1 to 6, wherein $R_1$ is cyclopentyl, cyclohexyl or cycloheptanyl, preferably cyclohexyl.

9. The peptide according to any one of 1 to 6, wherein $R_1$ is $C_5$ or $C_6$ aryl, preferably phenyl.

10. The peptide according to any one of 1 to 6, wherein $R_1$ is a group having the following formula:

11. The peptide according to any one of 1 to 5, wherein X is —NH— and $R_1$ is —CH(R)—COOH.

12. The peptide according to 1, wherein the peptide is selected from a peptide of the following table, wherein each of $Trp_{30}$, X and $R_1$ are selected as outlined therein:

| C-Modified Protoxin II Peptide | SEQ ID NO: | $Trp_{30}$ | X | $R_1$ |
|---|---|---|---|---|
| Protoxin II-NHMe | 11 | L-$Trp_{30}$ | —NH— | $—CH_3$ |
| Protoxin II-OMe | 12 | L-$Trp_{30}$ | —O— | $—CH_3$ |
| Protoxin II-NHcyclohexyl | 13 | L-$Trp_{30}$ | —NH— |  |
| Protoxin II (D)-NHcyclohexyl | 14 | D-$Trp_{30}$ | —NH— |  |
| Protoxin II-NHaniline | 15 | L-$Trp_{30}$ | —NH— |  |
| Protoxin II-D-Trp | 16 | L-$Trp_{30}$ | —NH— |  |

13. A peptide according to any one of 1 to 12 for use in a method for treatment of the human or animal body by therapy.

14. A peptide according to any one of 1 to 12 for use in treating pain.

15. Use of a peptide according to any one of 1 to 12 in the manufacture of a medicament for treating pain.

16. The peptide for use according to 14 or the use according to 15, wherein said pain treatment is prophylactically or therapeutically.

17. The peptide for use according to 14 or the use according to 15, wherein said pain is selected from the group consisting of neuropathic pain, chronic pain, acute pain, inflammatory pain and surgical pain.

18. An in vitro method of selectively blocking sodium channel Na$_v$1.7 in a cell, comprising contacting a cell expressing Na$_v$1.7 with at least one peptide according to 1 to 12.

19. An in vitro method of modulating the activity of sodium channel Na$_v$1.7 in a cell, or in a membrane preparation, comprising contacting said cell or said membrane preparation with at least one peptide according to 1 to 12.

---

The invention claimed is:

1. A C-terminal modified Protoxin II peptide of general formula (I):

$$(I)$$

wherein:
Pro is Protoxin II of the amino acid sequence: $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Glu_{12}$-$Arg_{13}$-$Lys_{14}$-$Cys_{15}$-$Cys_{16}$-$Glu_{17}$-$Gly_{18}$-$Met_{19}$-$Val_{20}$-$Cys_{21}$-$Arg_{22}$-$Leu_{23}$-$Trp_{24}$-$Cys_{25}$-$Lys_{26}$-$Lys_{27}$-$Lys_{28}$-$Leu_{29}$-$Trp_{30}$ (SEQ ID NO: 1),
wherein $Trp_{30}$ is D or L-$Trp_{30}$,
X is —NH—,
$R_1$ is $C_1$-$C_6$ alkyl, $C_3$-$C_7$ cycloalkyl, $C_5$-$C_{10}$ aryl, —CH(R)—COOH, wherein R is selected from a group consisting of —H, —$CH_3$, —$CH_2CH_2CH_2$—NH—C($NH_2$)=NH, —$CH_2CONH_2$, —$CH_2COOH$, —$CH_2CH_2COOH$, —$CH_2SH$, —$CH_2CH_2CONH_2$, —$CH(CH_3)CH_2CH_3$, —$CH_2CH(CH_3)_2$, —$CH(CH_3)_2$, —$CH_2CH_2CH_2NH_2$, —$CH_2CH_2SCH_3$, —$CH_2C_6H_6$, —$CH_2OH$, —$CH(OH)CH_3$, , , and

, or a pharmaceutically acceptable salt, or solvate thereof.

2. The peptide of claim 1 or a pharmaceutically acceptable salt, or solvate thereof, wherein $Trp_{30}$ is L-Trp.

3. The peptide of claim 1 or a pharmaceutically acceptable salt, or solvate thereof, wherein $Trp_{30}$ is D-Trp.

4. The peptide of claim 1 or a pharmaceutically acceptable salt, or solvate thereof, wherein $R_1$ is $C_1$-$C_4$ alkyl.

5. The peptide of claim 1 or a pharmaceutically acceptable salt, or solvate thereof, wherein $R_1$ is methyl, ethyl or propyl.

6. The peptide of claim 1 or a pharmaceutically acceptable salt, or solvate thereof, wherein $R_1$ is methyl.

7. The peptide of claim 1 or a pharmaceutically acceptable salt, or solvate thereof, wherein $R_1$ is cyclopentyl, cyclohexyl or cycloheptanyl.

8. The peptide of claim 1 or a pharmaceutically acceptable salt, or solvate thereof, wherein $R_1$ is cyclohexyl.

9. The peptide of claim 1 or a pharmaceutically acceptable salt, or solvate thereof, wherein $R_1$ is $C_5$ or $C_6$ aryl.

10. The peptide of claim 1 or a pharmaceutically acceptable salt, or solvate thereof, wherein $R_1$ is phenyl.

11. The peptide of claim 1 or a pharmaceutically acceptable salt, or solvate thereof, wherein $R_1$ is a group having the following formula:

12. The peptide of claim 1 or a pharmaceutically acceptable salt, or solvate thereof, wherein each of $Trp_{30}$, X and $R_1$ is listed in the following table:

| C-Modified Protoxin II Peptide | SEQ ID NO: | $Trp_{30}$ | X | $R_1$ |
|---|---|---|---|---|
| Protoxin II-NHMe | 11 | L-$Trp_{30}$ | —NH— | —$CH_3$ |
| Protoxin II-NHcyclohexyl | 13 | L-$Trp_{30}$ | —NH— | cyclohexyl |
| Protoxin II (D)-NHcyclohexyl | 14 | D-$Trp_{30}$ | —NH— | cyclohexyl |
| Protoxin II-NHaniline | 15 | L-$Trp_{30}$ | —NH— | phenyl |
| Protoxin II-D-Trp | 16 | L-$Trp_{30}$ | —NH— | D-Trp group |

13. The peptide of claim 1 or a pharmaceutically acceptable salt, or solvate thereof, wherein said peptide has a higher potency to $Na_v1.7$ as compared to unmodified Protoxin II measured by Fluorometric Imaging Plate Reader Assays or Electrophysiology Assay.

14. A pharmaceutical composition, comprising at least one C-terminal modified Protoxin II peptide of claim 1 or a pharmaceutically acceptable salt, or solvate thereof, and a pharmaceutically acceptable carrier.

15. A method of therapeutically treating pain, comprising administering an effective amount of at least one C-terminal modified Protoxin II peptide of claim 1 or a pharmaceutically acceptable salt, or solvate thereof, to a subject in need thereof.

16. The method of claim 15, wherein said pain is neuropathic pain, chronic pain, acute pain, inflammatory pain, or surgical pain.

17. A method of selectively blocking sodium channel $Na_v1.7$ in a cell, comprising contacting a cell expressing $Na_v1.7$ with at least one C-terminal modified Protoxin II peptide of claim 1, or a pharmaceutically acceptable salt, or solvate thereof.

18. The method of according to claim 17, wherein said C-terminal modified Protoxin II peptide has a selectivity for $Na_v1.7$ over $Na_v1.2$ defined by $Na_v1.7$ $IC_{50}/Na_v1.2$ $IC_{50}$ ratio of about 1/2, 1/3, 1/4, 1/5, 1/6, 1/7, 1/8, 1/9, 1/10, 1/15, 1/20, 1/25, 1/30, 1/35, 1/40, 1/45, 1/50, 1/55, 1/60, 1/65, 1/70, 1/75, 1/80, 1/85, 1/90, 1/95, 1/100, 1/125, 1/150, 1/175, 1/200, 1/225, 1/250, 1/275, 1/300, 1/325, 1/350, 1/375, 1/400, 1/425, 1/450, 1/475 or 1/500 or less.

19. A method of modulating the activity of sodium channel $Na_v1.7$ in a cell, or in a membrane preparation, comprising contacting said cell or said membrane preparation with an effective amount of at least one C-terminal modified Protoxin II peptide of claim 1, or a pharmaceutically acceptable salt, or solvate thereof.

* * * * *

```
                         SEQUENCE LISTING

<160> NUMBER OF SEQ ID NOS: 16

<210> SEQ ID NO 1
<211> LENGTH: 30
<212> TYPE: PRT
<213> ORGANISM: Thrixopelma pruriens
<220> FEATURE:
<223> OTHER INFORMATION: Protoxin II

<400> SEQUENCE: 1

Tyr Cys Gln Lys Trp Met Trp Thr Cys Asp Ser Glu Arg Lys Cys Cys
1               5                   10                  15

Glu Gly Met Val Cys Arg Leu Trp Cys Lys Lys Lys Leu Trp
            20                  25                  30

<210> SEQ ID NO 2
<211> LENGTH: 29
<212> TYPE: PRT
<213> ORGANISM: Grammostola spatulata
<220> FEATURE:
<223> OTHER INFORMATION: Phrixotoxin I

<400> SEQUENCE: 2

Tyr Cys Gln Lys Trp Met Trp Thr Cys Asp Ser Ala Arg Lys Cys Cys
1               5                   10                  15

Glu Gly Leu Val Cys Arg Leu Trp Cys Lys Lys Ile Ile
            20                  25

<210> SEQ ID NO 3
<211> LENGTH: 29
<212> TYPE: PRT
<213> ORGANISM: Chilobrachys jingzhao
<220> FEATURE:
<223> OTHER INFORMATION: JzTx XII

<400> SEQUENCE: 3

Tyr Cys Gln Lys Trp Met Trp Thr Cys Asp Ser Glu Arg Lys Cys Cys
1               5                   10                  15

Glu Gly Tyr Val Cys Glu Leu Trp Cys Lys Tyr Asn Leu
            20                  25

<210> SEQ ID NO 4
<211> LENGTH: 29
<212> TYPE: PRT
<213> ORGANISM: Grammostola spatulata
<220> FEATURE:
<223> OTHER INFORMATION: GsAF I

<400> SEQUENCE: 4

Tyr Cys Gln Lys Trp Leu Trp Thr Cys Asp Ser Glu Arg Lys Cys Cys
1               5                   10                  15

Glu Asp Met Val Cys Arg Leu Trp Cys Lys Lys Arg Leu
            20                  25

<210> SEQ ID NO 5
<211> LENGTH: 29
<212> TYPE: PRT
<213> ORGANISM: Chilobrachys jingzhao
<220> FEATURE:
<223> OTHER INFORMATION: JzTx V
```

```
<400> SEQUENCE: 5

Tyr Cys Gln Lys Trp Met Trp Thr Cys Asp Ser Lys Arg Ala Cys Cys
1               5                   10                  15

Glu Gly Leu Arg Cys Lys Leu Trp Cys Arg Lys Ile Ile
            20                  25

<210> SEQ ID NO 6
<211> LENGTH: 32
<212> TYPE: PRT
<213> ORGANISM: Grammostola rosea
<220> FEATURE:
<223> OTHER INFORMATION: VsTx II

<400> SEQUENCE: 6

Tyr Cys Gln Lys Trp Met Trp Thr Cys Asp Glu Glu Arg Lys Cys Cys
1               5                   10                  15

Glu Gly Leu Val Cys Arg Leu Trp Cys Lys Lys Lys Ile Glu Glu Gly
            20                  25                  30

<210> SEQ ID NO 7
<211> LENGTH: 31
<212> TYPE: PRT
<213> ORGANISM: Grammostola spatulata
<220> FEATURE:
<223> OTHER INFORMATION: GsAF II

<400> SEQUENCE: 7

Tyr Cys Gln Lys Trp Met Trp Thr Cys Asp Glu Glu Arg Lys Cys Cys
1               5                   10                  15

Glu Gly Leu Val Cys Arg Leu Trp Cys Lys Lys Lys Ile Glu Trp
            20                  25                  30

<210> SEQ ID NO 8
<211> LENGTH: 29
<212> TYPE: PRT
<213> ORGANISM: Grammostola spatulata
<220> FEATURE:
<223> OTHER INFORMATION: GrTx I

<400> SEQUENCE: 8

Tyr Cys Gln Lys Trp Met Trp Thr Cys Asp Ser Lys Arg Lys Cys Cys
1               5                   10                  15

Glu Asp Met Val Cys Gln Leu Trp Cys Lys Lys Arg Leu
            20                  25

<210> SEQ ID NO 9
<211> LENGTH: 31
<212> TYPE: PRT
<213> ORGANISM: Grammostola spatulata
<220> FEATURE:
<223> OTHER INFORMATION: GsMtx II / PaTx II

<400> SEQUENCE: 9

Tyr Cys Gln Lys Trp Met Trp Thr Cys Asp Glu Glu Arg Lys Cys Cys
1               5                   10                  15

Glu Gly Leu Val Cys Arg Leu Trp Cys Lys Arg Ile Ile Asn Met
            20                  25                  30

<210> SEQ ID NO 10
<211> LENGTH: 30
<212> TYPE: PRT
<213> ORGANISM: Artificial Sequence
<220> FEATURE:
```

```
<223> OTHER INFORMATION: Protoxin II with amidated C-terminus
<220> FEATURE:
<221> NAME/KEY: MOD_RES
<222> LOCATION: (30)..(30)
<223> OTHER INFORMATION: amidated C-terminus

<400> SEQUENCE: 10

Tyr Cys Gln Lys Trp Met Trp Thr Cys Asp Ser Glu Arg Lys Cys Cys
1               5                   10                  15

Glu Gly Met Val Cys Arg Leu Trp Cys Lys Lys Lys Leu Trp
            20                  25                  30

<210> SEQ ID NO 11
<211> LENGTH: 30
<212> TYPE: PRT
<213> ORGANISM: Artificial Sequence
<220> FEATURE:
<223> OTHER INFORMATION: Protoxin II with C-terminus amidated with
      aminomethyl
<220> FEATURE:
<221> NAME/KEY: MOD_RES
<222> LOCATION: (30)..(30)
<223> OTHER INFORMATION: C-terminus amidated with aminomethyl

<400> SEQUENCE: 11

Tyr Cys Gln Lys Trp Met Trp Thr Cys Asp Ser Glu Arg Lys Cys Cys
1               5                   10                  15

Glu Gly Met Val Cys Arg Leu Trp Cys Lys Lys Lys Leu Trp
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: Protoxin II with methylester at C-terminus
<220> FEATURE:
<221> NAME/KEY: MOD_RES
<222> LOCATION: (30)..(30)
<223> OTHER INFORMATION: Methylester at C-terminus

<400> SEQUENCE: 12

Tyr Cys Gln Lys Trp Met Trp Thr Cys Asp Ser Glu Arg Lys Cys Cys
1               5                   10                  15

Glu Gly Met Val Cys Arg Leu Trp Cys Lys Lys Lys Leu Trp
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: Protoxin II with C-terminus amidated with
      NH-cyclohexyl
<220> FEATURE:
<221> NAME/KEY: MOD_RES
<222> LOCATION: (30)..(30)
<223> OTHER INFORMATION: C-terminus amidated with NH-cyclohexyl

<400> SEQUENCE: 13

Tyr Cys Gln Lys Trp Met Trp Thr Cys Asp Ser Glu Arg Lys Cys Cys
1               5                   10                  15

Glu Gly Met Val Cys Arg Leu Trp Cys Lys Lys Lys Leu Trp
            20                  25                  30

<210> SEQ ID NO 14
<211> LENGTH: 30
```

```
<212> TYPE: PRT
<213> ORGANISM: Artificial Sequence
<220> FEATURE:
<223> OTHER INFORMATION: Protoxin II with C-terminus amidated with
      NH-cyclohexyl; Trp 30 is in D-configuration
<220> FEATURE:
<221> NAME/KEY: MOD_RES
<222> LOCATION: (30)..(30)
<223> OTHER INFORMATION: C-terminus amidated with NH-cyclohexyl
<220> FEATURE:
<221> NAME/KEY: MISC_FEATURE
<222> LOCATION: (30)..(30)
<223> OTHER INFORMATION: D-Trp

<400> SEQUENCE: 14

Tyr Cys Gln Lys Trp Met Trp Thr Cys Asp Ser Glu Arg Lys Cys Cys
1               5                   10                  15

Glu Gly Met Val Cys Arg Leu Trp Cys Lys Lys Lys Leu Trp
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: Protoxin II C-terminus amidated with aniline
<220> FEATURE:
<221> NAME/KEY: MOD_RES
<222> LOCATION: (30)..(30)
<223> OTHER INFORMATION: C-terminus amidated wth aniline

<400> SEQUENCE: 15

Tyr Cys Gln Lys Trp Met Trp Thr Cys Asp Ser Glu Arg Lys Cys Cys
1               5                   10                  15

Glu Gly Met Val Cys Arg Leu Trp Cys Lys Lys Lys Leu Trp
            20                  25                  30

<210> SEQ ID NO 16
<211> LENGTH: 31
<212> TYPE: PRT
<213> ORGANISM: Artificial Sequence
<220> FEATURE:
<223> OTHER INFORMATION: Protoxin II with additional D-Trp at C-terminus
<220> FEATURE:
<221> NAME/KEY: misc_feature
<222> LOCATION: (31)..(31)
<223> OTHER INFORMATION: D-Trp

<400> SEQUENCE: 16

Tyr Cys Gln Lys Trp Met Trp Thr Cys Asp Ser Glu Arg Lys Cys Cys
1               5                   10                  15

Glu Gly Met Val Cys Arg Leu Trp Cys Lys Lys Lys Leu Trp Trp
            20                  25                  30
```